US00RE39897E

(19) United States
(12) Reissued Patent
Mower

(10) Patent Number: US RE39,897 E
(45) **Date of Reissued Patent: *Oct. 23, 2007**

(54) METHOD AND APPARATUS FOR TREATING HEMODYNAMIC DISFUNCTION

(75) Inventor: Morton M. Mower, Baltimore, MD (US)

(73) Assignee: Mirowski Family Ventures, L.L.C., Washington, DC (US)

( * ) Notice: This patent is subject to a terminal disclaimer.

(21) Appl. No.: 10/214,474

(22) Filed: Aug. 8, 2002

Related U.S. Patent Documents

Reissue of:
(64) Patent No.: 4,928,688
Issued: May 29, 1990
Appl. No.: 07/299,895
Filed: Jan. 23, 1989

U.S. Applications:
(63) Continuation of application No. 08/547,691, filed on Oct. 19, 1995, now Pat. No. Re. 38,119, which is a continuation of application No. 07/890,280, filed on May 29, 1992, now abandoned.

(51) Int. Cl.
*A61N 1/362* (2006.01)

(52) U.S. Cl. ..... 607/9

(58) Field of Classification Search ..... 607/4.28

See application file for complete search history.

(56) References Cited

U.S. PATENT DOCUMENTS

| | | | |
|---|---|---|---|
| 3,345,990 | A | 10/1967 | Berkovits |
| 3,431,912 | A | 3/1969 | Keller, Jr. |
| 3,433,228 | A | 3/1969 | Keller, Jr. |

(Continued)

FOREIGN PATENT DOCUMENTS

| | | | |
|---|---|---|---|
| DE | 2119255 | A | 7/1975 |
| DE | 1401247 | | 11/1983 |
| EP | 0017447 | A1 | 10/1980 |
| EP | 0039269 | A1 | 11/1981 |
| WO | WO 82/03783 | | 11/1982 |

OTHER PUBLICATIONS

Updated Case Docket for *Medtronic, Inc.* v. *Guidant Corp.*, No. 03–848–SLR (D. Del.)

Case Docket for *Medtronic, Inc.* v. *Guidant Corp.*, No. 05–1515 (Fed. Cir.) appealed from *Medtronic, Inc.* v.*Guidant Corp.*, No. 03–848–SLR (D. Del.).

Brief for Plaintiff–Appellant Medtronic, Inc. filed Oct. 28, 2005 in *Medtronic, Inc.* v. *Guidant Corp.*, No. 05–1515 (Fed. Cir.).

(Continued)

*Primary Examiner*—Scott M. Getzow
(74) *Attorney, Agent, or Firm*—Finnegan, Henderson, Farabow, Garrett & Dunner, L.L.P.

(57) ABSTRACT

A method of treating hemodynamic disfunction by simultaneously pacing both ventricles of a heart. At least one ECG amplifier is arranged to separately detect contraction of each ventricle and a stimulator is then activated for issuing stimulating pulses to both ventricles in a manner to assure simultaneous contraction of both ventricles, thereby to assure hemodynamic efficiency. A first ventricle is stimulated simultaneously with contraction of a second ventricle when the first fails to properly contract. Further, both ventricles are stimulated after lapse of a predetermined A-V escape interval. One of a pair of electrodes, connected in series, in placed through the superior vena cava into the right ventricle and a second is placed in the coronary sinus about the left ventricle. Each electrode performs both pacing and sensing functions. The pacer is particularly suitable for treating bundle branch blocks or slow conduction in a portion of the ventricles.

317 Claims, 2 Drawing Sheets

U.S. PATENT DOCUMENTS

Figure 1:
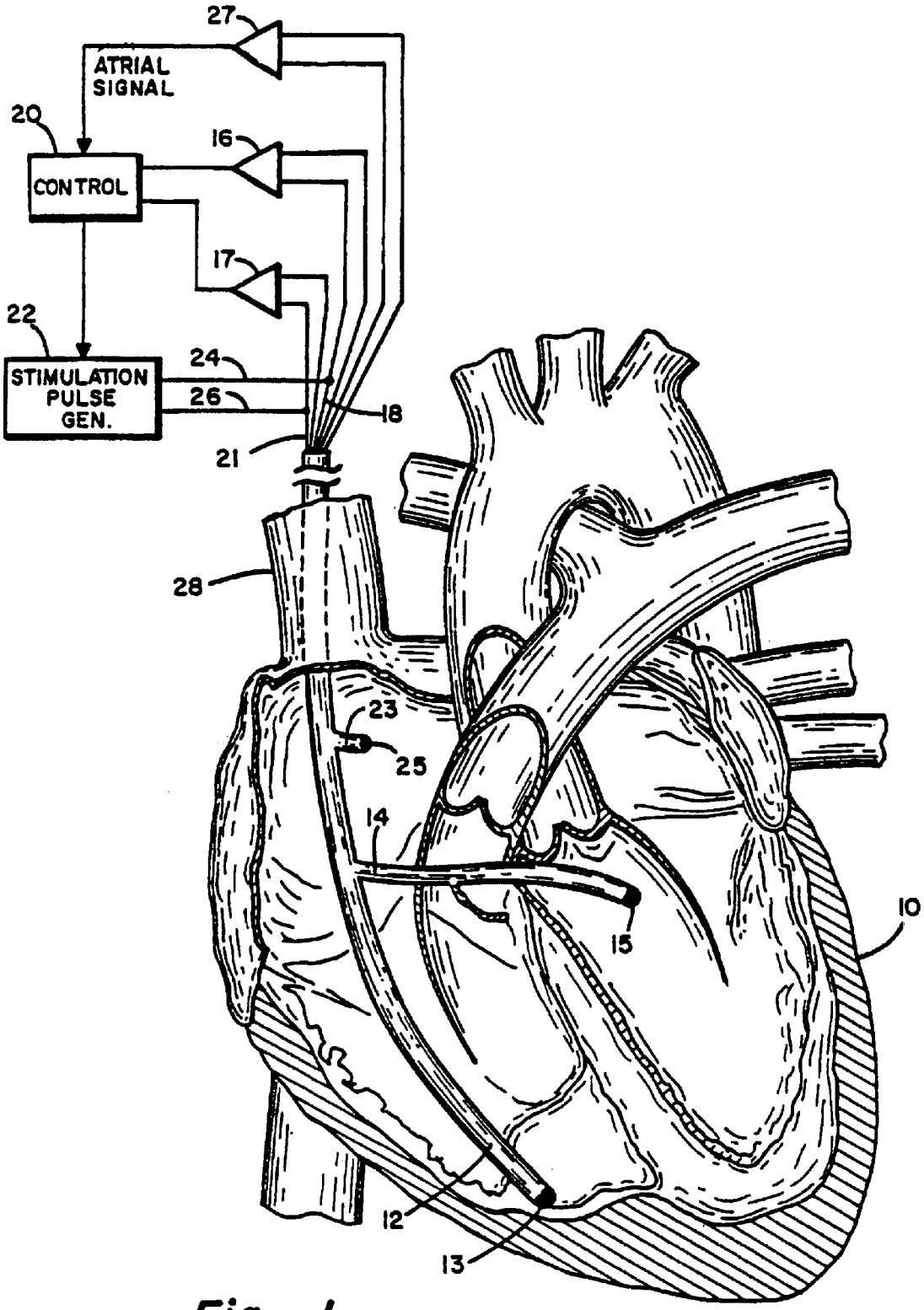

| | | | | |
|---|---|---|---|---|
| 3,595,242 | A | | 7/1971 | Berkovits |
| 3,648,707 | A | | 3/1972 | Greatbach |
| 3,747,604 | A | | 7/1973 | Berkovits |
| 3,814,106 | A | | 6/1974 | Berkovits |
| 3,903,897 | A | | 9/1975 | Woolons et al. |
| 3,937,226 | A | | 2/1976 | Funke |
| 4,052,991 | A | | 10/1977 | Zacouto |
| 4,057,067 | A | | 11/1977 | Lajos |
| 4,088,140 | A | | 5/1978 | Rockland et al. |
| 4,303,075 | A | | 12/1981 | Heilman et al. |
| 4,312,355 | A | | 1/1982 | Funke |
| 4,332,259 | A | | 6/1982 | McCorkle, Jr. |
| 4,335,727 | A | | 6/1982 | McPherson |
| 4,354,497 | A | | 10/1982 | Kahn |
| 4,378,020 | A | * | 3/1983 | Nappholz et al. |
| 4,386,610 | A | | 6/1983 | Leckrone |
| 4,401,119 | A | | 8/1983 | Herpers |
| 4,418,695 | A | | 12/1983 | Buffet |
| 4,429,697 | A | | 2/1984 | Nappholz et al. |
| 4,452,248 | A | | 6/1984 | Keller, Jr. |
| 4,458,677 | A | | 7/1984 | McCorkle, Jr. |
| 4,541,417 | A | | 9/1985 | Krikorian |
| 4,548,203 | A | | 10/1985 | Tacker, Jr. et al. |
| 4,554,922 | A | | 11/1985 | Prystowsky et al. |
| 4,559,946 | A | | 12/1985 | Mower |
| 4,624,260 | A | | 11/1986 | Baker, Jr. et al. |
| 4,685,446 | A | | 8/1987 | Choy |
| 4,705,043 | A | | 11/1987 | Imran |
| 4,727,877 | A | | 3/1988 | Kallok |
| 4,774,950 | A | | 10/1988 | Cohen |
| 4,790,317 | A | | 12/1988 | Davies |
| 4,799,486 | A | | 1/1989 | DuFault |
| 4,817,608 | A | | 4/1989 | Shapland et al. |
| 4,827,932 | A | | 5/1989 | Ideker et al. |
| 4,827,934 | A | | 5/1989 | Ekwall |
| 4,830,006 | A | | 5/1989 | Haluska et al. |
| 4,925,443 | A | | 5/1990 | Heilman et al. |
| 4,932,407 | A | | 6/1990 | Williams |
| 4,958,632 | A | | 9/1990 | Duggan |
| 4,967,749 | A | | 11/1990 | Cohen |
| 4,974,588 | A | | 12/1990 | Smits |
| 5,014,696 | A | | 5/1991 | Mehra |
| 5,024,222 | A | | 6/1991 | Thacker |
| 5,083,563 | A | | 1/1992 | Collins |
| 5,099,838 | A | | 3/1992 | Bardy |
| 5,111,811 | A | | 5/1992 | Smits |
| 5,129,394 | A | | 7/1992 | Mehra |
| 5,158,097 | A | | 10/1992 | Christlieb |
| 5,213,098 | A | | 5/1993 | Bennett et al. |
| 5,251,621 | A | | 10/1993 | Collins |
| 5,334,222 | A | | 8/1994 | Salo et al. |
| 5,545,204 | A | | 8/1996 | Cammilli et al. |
| 5,584,868 | A | | 12/1996 | Salo et al. |
| 5,626,620 | A | | 5/1997 | Kieval et al. |
| 5,755,766 | A | | 5/1998 | Chastain et al. |
| 5,899,930 | A | | 5/1999 | Flynn et al. |
| 5,902,324 | A | | 5/1999 | Thompson et al. |
| 5,919,209 | A | | 7/1999 | Schouten |
| 5,935,160 | A | | 8/1999 | Auricchio et al. |
| 6,185,459 | B1 | | 2/2001 | Mehra et al. |

OTHER PUBLICATIONS

Brief of Defendants–Appellees Guidant Corporation, Guidant Sales Corporation, Eli Lilly & Company, and Mirowski Family Ventures LLC filed Jan. 11, 2006 in *Medtronic, Inc.* v. *Guidant Corp.*, No. 05–1515 (Fed. Cir.).

Reply Brief for Plaintiff–Appellant Medtronic, Inc. filed Feb. 8, 2006 in *Medtronic, Inc.* v. *Guidant Corp.*, No. 05–1515 (Fed. Cir.).

Motion of St. Jude Medical, Inc. For Leave to File Brief as *Amicus Curiae* filed Nov. 8, 2005 in *Medtronic, Inc.* v. *Guidant Corp.*, No. 05–1515 (Fed. Cir.).

Brief for St. Jude Medical, Inc., as *Amicus Curiae* Supporting Appellant filed Nov. 8, 2005 in *Medtronic, Inc.* v. *Guidant Corp.*, No. 05–1515 (Fed. Cir.).

Updated Case Docket for *Guidant Corp.* v. *St. Jude Medical, Inc.*, No. 04–0067–SLR (D. Del.).

Plaintiffs' (Guidant et al.) Motion for Leave to File a Surreply from *Guidant Corp.* v. *St. Jude Medical, Inc.*, No. 04–0067–SLR (D. Del.).

Defendants' (St. Jude et al.) Opposition to Plaintiffs' (Guidant et al.) Motion for Leave to File a Surreply from *Guidant Corp.* v. *St. Jude Medical, Inc.*, No. 04–0067–SLR (D. Del.).

Defendants' (St. Jude et al.) Request for Oral Argument from *Guidant Corp.* v. *St. Jude Medical,Inc.* , No. 04–0067–SLR (D. Del.).

Plaintiffs' (Guidant et al.) Opposition to St. Jude's Request for Oral Argument from *Guidant Corp.* v. *St. Jude Medical, Inc.*, No. 04–0067–SLR (D. Del.).

Plaintiffs' (Guidant et al.) Reply to St. Jude's Opposition to Plaintiffs' (Guidant et al.) Motion for Leave to File a Surreply from *Guidant Corp.* v. *St. Jude Medical, Inc.*, No. 04–0067–SLR (D. Del.).

Memorandum Opinion dated Jan. 6, 2006 denying Defendants' (St. Jude et al.) Motion for Summary Judgment of Invalidity Based on Reissue Recapture issued in *Guidant Corp.* v. *St. Jude Medical, Inc.*, No. 04–0067–SLR (D. Del.).

Defendants' (St. Jude et al.) Supplemental Initial Disclosures (Documents) from *Guidant Corp.* v. *St. Jude Medical, Inc.*, No. 04–0067–SLR (D. Del.).

Plaintiffs' (Guidant et al.) Additional Supplemental Responses to Defendants' (St. Jude et al.) First, Second, and Third Sets of Interrogatories (1–35).

Plaintiffs' (Guidant et al.) Responses to Defendants' (St. Jude et al.) Fourth Set of Interrogatories (36–40) from *Guidant Corp.* v. *St. Jude Medical, Inc.*, No. 04–0067–SLR (D. Del.).

Plaintiffs' (Guidant et al.) Third Supplemental Response to Defendants' (St. Jude et al.) Interrogatory No. 1 from *Guidant Corp.* v. *St. Jude Medical, Inc.*, No. 04–0067–SLR (D. Del.).

Defendants' (St. Jude et al.) Supplemental Response to Plaintiffs' (Guidant et al.) Fourth Set of Interrogatories (No. 19) from *Guidant Corp.* v. *St. Jude Medical, Inc.*, No. 04–0067–SLR (D. Del.).

Plaintiffs' (Guidant et al.) Responses to Defendants' (St. Jude et al.) Second Set of Requests for Admissions (27–38) from *Guidant Corp.* v. *St. Jude Medical, Inc.*, No. 04–0067–SLR (D. Del.).

Transcript of the Deposition of Morton M. Mower, M.D., taken Oct. 17, 2005 in *Guidant Corp.* v. *St. Jude Medical, Inc.*, No. 04–0067–SLR (D. Del.).

Transcript of the Deposition of Morton M. Mower, M.D., taken Oct. 18, 2005 in *Guidant Corp.* v. *St. Jude Medical, Inc.*, No. 04–0067–SLR (D. Del.).

Curriculum Vitae of Dr. Morton M. Mower (Exhibit 90 of the Deposition of Dr. Morton M. Mower, M.D., taken Oct. 17–18, 2005).

Materials related to the Mirowski Symposium (Exhibit 93 of the Deposition of Dr. Morton M. Mower, M.D., taken Oct. 17–18, 2005.

Document entitled "Bibliography 35. What's New?" (Exhibit 94 of the Deposition of Dr. Morton M. Mower, M.D., taken Oct. 17–18, 2005).
Letter from M. Mower to S. Barold (Exhibit 95 of the Deposition of Dr. Morton M. Mower, M.D., taken Oct. 17–18, 2005).
Letter from S. Rickerson to T. Nikolai dated Oct. 30, 1987 (Exhibit 102 of the Deposition of Dr. Morton M. Mower, M.D., taken Oct. 17–18, 2005).
Document entitled "New Idea" (Exhibit 103 of the Deposition of Dr. Morton M. Mower, M.D., taken Oct. 17–18, 2005).
Letter from T. Nikolai to M. Mower dated Dec. 3, 1987 (Exhibit 104 of the Deposition of Dr. Morton M. Mower, M.D., taken Oct. 17–18, 2005).
Letter from R. Cohn to T. Nikolai dated Aug. 23, 1988 (Exhibit 105 of the Deposition of Dr. Morton M. Mower, M.D., taken Oct. 17–18, 2005).
Letter from T. Nikolai to M. Mower dated Aug. 31, 1988 (Exhibit 106 of the Deposition of Dr. Morton M. Mower, M.D., taken Oct. 17–18, 2005).
Fax from J. Heemels to J. Spinelli dated Feb. 21, 1992 (Exhibit 109 of the Deposition of Dr. Morton M. Mower, M.D., taken Oct. 17–18, 2005).
Fax from M. Mower to J. Millerhagen (Exhibit 110 of the Deposition of Dr. Morton M. Mower, M.D., taken Oct. 17–18, 2005).
Presentation bearing bates Nos. MM0247–51 (Exhibit 124 of the Deposition of Dr. Morton M. Mower, M.D., taken Oct. 17–18, 2005).
Presentation bearing bates Nos. MM0278–342 (Exhibit 125 of the Deposition of Dr. Morton M. Mower, M.D., taken Oct. 17–18, 2005).
Presentation bearing bates Nos. MM0013–79 (Exhibit 126 of the Deposition of Dr. Morton M. Mower, M.D., taken Oct. 17–18, 2005).
Presentation entitled "A History of ICD & Related Therapies" and bearing bates Nos. MM0087–139 (Exhibit 127 of the Deposition of Dr. Morton M. Mower, M.D., taken Oct. 17–18, 2005).
Presentation entitled "Cardiac Resynchronization Therapy (CRT) Reduces Hospitalizations, and CRT with Implantable Defibrillator (CRT–D) Reduces Mortality in Chronic Heart Failure: The Companion Trial" and bearing bates Nos. MM0257–77 (Exhibit 128 of the Deposition of Dr. Morton M. Mower, M.D., taken Oct. 17–18, 2005).
Presentation bearing bates Nos. MM0343–401 (Exhibit 129 of the Deposition of Dr. Morton M. Mower, M.D., taken Oct. 17–18, 2005).
Presentation entitled "Evolution of Cardiac Rhythm Management Systems: A History of Automatic Implantable Cardioverter–Defibrillator (AICD)" and bearing bates Nos. MM0402–454 (Exhibit 130 of the Deposition of Dr. Morton M. Mower, M.D., taken Oct. 17–18, 2005).
Presentation bearing bates Nos. MM0508–692 (Exhibit 131 of the Deposition of Dr. Morton M. Mower, M.D., taken Oct. 17–18, 2005).
Document bearing bates Nos. A0095–108 (Exhibit 133 of the Deposition of Dr. Morton M. Mower, M.D., taken Oct. 17–18, 2005).
Document showing Biventricular Pacer of American Optical Co. (Exhibit 143 of the Deposition of Dr. Morton M. Mower, M.D., taken Oct. 17–18, 2005).
Document dated Jul. 20, 1988 and bearing bates Nos. GDT2800–02 (Exhibit 146 of the Deposition of Dr. Morton M. Mower, M.D., taken Oct. 17–18, 2005).
Transcript of the Deposition of Dr. Barouh V. Berkovits, taken Dec. 7, 2005 in *Guidant Corp.* v. *St. Jude Medical, Inc.*, No. 04–0067–SLR (D. Del.).
Transcript of the Deposition of Julio Spinelli, taken Nov. 10, 2005 in *Guidant Corp.* v. *St. Jude Medical, Inc.*, No. 04–0067–SLR (D. Del.).
Email from J. Spinelli to A. Kadish dated Aug. 2, 2005 (Ex. 222 of the Deposition of Julio Spinelli, taken Nov. 10, 2005).
Summary of Expected Testimony of David G. Benditt, MD, FACC, FRCP(C), FHRS, (Expert for St. Jude, et al.) from *Guidant Corp.* v. *St. Jude Medical, Inc.*, No. 04–0067–SLR (D. Del.) (With Accompanying Exhibits A–C).
Expert Report of Eduardo De Teresa Galván (Expert for St. Jude, et al.) from *Guidant Corp.* v. *St. Jude Medical, Inc.*, No. 04–0067–SLR (D. Del.) With Accompanying Exhibits A–B).
Expert Report of Harry F. Manbeck, Jr. (Expert for St. Jude, et al.) from *Guidant Corp.* v. *St. Jude Medical, Inc.*, No. 04–0067–SLR (D. Del.) (With Accompanying Exhibits A–D).
Expert Report of Kimberly A. Moore (Expert for St. Jude, et al.) from *Guidant Corp.* v. *St. Jude Medical, Inc.*, No. 04–0067–SLR (D. Del.) (With Accompanying Exhibit A).
Abraham, WT, et al., "Cardiac Resynchronization in Chronic Heart Failure," *N. Engl. J. Med.*, vol. 346, No. 24, 2002, pp. 1845–1853.
Anagnostopoulos, CE, et al., "Transvenous Coronary Sinus Pacemaker: A New Primary Approach to Heart Block in Patients with Tricuspid Prostheses," *The Annals of Thoracic Surgery*, vol. 9, No. 3, Mar. 1970, pp. 248–252.
Aurrichio A, et al, "Effect of Pacing Chamber and Atrioventricular Delay on Acute Systolic Function of Paced Patients With Congestive Heart Failure," *Circulation*, vol. 99, No. 23, Jun. 1999, pp. 2993–3001.
Aurrichio A, et al., "Long–Term Clinical Effect of Hemodynamically Optimized Cardiac Resynchronization Therapy in Patients With Heart Failure and Ventricular Conduction Delay," *J. Am. Coll. Cardiol.*, vol. 39, No. 12, 2002, pp. 2026–2033.
Befeler, B, et al., "Cardiovascular Dynamics During Coronary Sinus, Right Atrial, and Right Ventricular Pacing," *Am. Heart J.*, vol. 81, No. 3, Mar. 1971, pp. 372–380.
Benditt, DG et al., "Sensor–Triggered Rate–Variable Cardiac Pacing: Current Technologies and Clinical Implications," *Annals of Internal Med.*, vol. 107, No. 5, Nov. 1987, pp. 714–724.
Berkovits, B, et al., "Bifocal Demand Pacing," *Singapore Med. J.*, vol. 14, No. 3, Sep. 1973, pp. 316–319.
Berkovits, B, "Demand Pacing," *Annals of New York Academy of Sciences*, vol. 167, Art. 2, Oct. 1969, pp. 891–895.
Berkovits, B., et al.., "Future Generation Pacemakers," *Pacemaker Therapy*, L. Dreifus ed., 1983, pp. 265–276.
Blanc JJ, et al., "Recurrent Supraventricular Tachycardia: The Efficacy of a Radio Frequency System Inserted into the Coronary Sinus," *Archives des Maladies du Coeur et des Vaisseaux*, 1978, 71:687–90.
Blanc JJ, et al., "Evaluation of Different Ventricular Pacing Sites in Patients With Severe Heart Failure: Results of an Acute Hemodynamic Study," *Circulation*, vol. 96, No. 10, Nov. 1997, pp. 3273–3277.

Blanc JJ, et al., "A Method for Permanent Transvenous Left Ventricular Pacing," *PACE*, vol. 21, Nov. 1998, pp. 2021–2024.

Bognolo, DA, "Recent Advances in Permanent Pacemaker Implantation Techniques," *Modern Cardiac Pacing*, Barold SS, ed., Futura Publishing Co., 1985, pp. 199–229.

Bristow MR, et al., "Cardiac–Resynchronization Therapy With or Without an Implantable Defibrillator in Advanced Chronic Heart Failure," *N. Engl. J. Med.*, vol. 350, 2004, 2140–50.

Burkoff, D, et al., "Influence of Pacing Site on Canine Left Ventricular Contraction," *Am. J. Physiol.* (*Heart Circ. Physiol.*), 1986:20:H428–H435.

Castellanos, A, et al., "Atrial Demand and AV Sequential Pacemakers," *Pacemaker Therapy*, L. Dreifus, ed., 1983, pp. 149–164.

Castellanos, A, et al., "Cardiac Pacemakers," *Cardiac Surgery 2*, vol. 3, No. 2, D. Harken, ed., 1971, pp. 32–44.

Castellanos, A, et al., "Effects of Pacemaker Impulses on Latent Arrhythmias Produced by Intramyocardial Chemical Stimulation," *Cardiologia*, vol. 51, No. 6, 1967, pp. 340–348.

Castellanos, A, et al., "An Electrical Digitalis Tolerance Test," *Am. J. of Medical Sciences*, Nov. 1967, pp. 159–168.

Castellanos, A, et al., "The Electrocardiogram and Vectorcardiogram of Ectopic Ventricular Beats," *Acta Cardiologica*, vol. 28, No. 6, 1973, pp. 562–575.

Castellanos, A, et al., "Electronic Pacemaker Models of Parasystole: With Special Reference to Artificial Intermittent Parasystole With Phase 3 and Phase 4 Protection and to Parasystolic Modulation," *PACE*, vol. 5, No. 4, Jul. 1982, pp. 537–545.

Castellanos, A, et al., "Evaluacion Clinica De Los Marcapasos Implantados, " *Boletin de la Associacion Medica de Puerto Rico*, vol. 73, No. 12, Dec. 1981, pp. 644–653.

Castellanos, A, et al., "His Bundle Recordings in Atrioventricular Nodal Alternating Wenckebach Periods Ending in 5:1 Atrioventricular Block Coexisting with Paroxysmal Atrioventricular Nodal Block," *CHEST*, vol. 74, No. 3, Sep. 1978, pp. 274–279.

Castellanos, A, et al., "Implantable Demand Pacemaker," *Brit. Heart J.*, vol. 30, 1968, pp. 29–33.

Castellanos, A, et al., "Implantable Pacemakers for Cardiac Tachyarrhythmias," *Cardiac Arrythmias: Mechanisms and Management*, A. Castellanos, ed., 1980, pp. 159–173.

Castellanos, A, et al., "A New Instrument for Automatic Monitoring and Tape Recording in Infants and Children," *Boletin de la Associacion Medica de Puerto Rico*, vol. 58, No. 7, Jul. 1966, pp. 355–359.

Castellanos, A., et al., "Pacemaker–Induced Cardiac Rhythm Disturbances," *Annals of New York Academy of Sciences*, vol. 167, No. 2, Oct. 1969, pp. 903–910.

Castellanos, A, et al., "Pacemaker Vectorcardiography," *Am. Heart J.*, vol. 75, No. 1, Jan. 1968, pp. 6–18.

Castellanos, A, et al., "Pacing in Acute Myocardial Infarction: A Programmed Introduction," *CHEST*, vol. 58, No. 2, Aug. 1970, pp. 152–163.

Castellanos, A, et al., "Preliminary Studies With an Implantable Multimodal A–V Pacemaker for Reciprocating Atrioventricular Tachycardias," *PACE*, vol. 3, No. 3, May 1980, pp. 257–265.

Castellanos, A, et al., "Repetitive Firing Occurring During Synchronized Electrical Stimulation of the Heart," *J. of Thoracic Cardiovascular Surgery*, vol. 51, No. 3, Mar. 1966, pp. 334–340.

Castellanos, A, et al., "Sextapolar Catheter Electrode for Temporary Sequential Atrioventricular Pacing," *Cardiovascular Research*, vol. 8, No. 5, Sep. 1974, pp. 712–714.

Castellanos, A, et al., "Significance of Multiple Responses Produced by Electrical Depolarization of the Heart," *Acta Cardiologica*, vol. 21, No. 2, 1966, pp. 157–166.

Castellanos, A., et al., "Simultaneous Biventricular Stimulation for Ventricular Arrhythmias," *Am. J. Cardiol*, vol. 88, Nov. 15, 2001, pp. 1217–1218.

Castellanos, A, et al., "A Study of Arrival of Excitation at Selected Ventricular Sites during Human Bundle Branch Block Using Close Bipolar Catheter Electrodes," *CHEST*, vol. 63, No. 2, Feb. 1973, pp. 208–213.

Castellanos, A, et al., "St–qR Pattern: New Sign for Diagnosis of Anterior Myocardial Infarction During Right Ventricular Pacing," *Br. Heart J.*, vol. 35, Oct. 1973, pp. 1161–1165.

Castellanos, A, et al., "The Use of the Demand Pacemaker in Auriculo–Ventricular Conduction Disturbances," *J. of Cardiovascular Surgery*, vol. 7, No. 2, Mar.–Apr. 1966, pp. 92–96.

Castellanos, A, et al., "Ventricular–triggered Pacemaker Arrhythmias," *Brit. Heart J.*, vol. 31, 1969, pp. 546–552.

Castellanos, A, et al., "The Wedensky Effect in the Human Heart," *Brit. Heart J.*, vol. 28, 1966, pp. 276–283.

Castillo, C, et al., "Bifocal Demand Pacing," *CHEST*, vol. 59, No. 4, Apr. 1971, pp. 360–364.

Cazeau S, et al., "Effects of Multisite Biventricular Pacing in Patients With Heart Failure and Intraventricular Conduction Delay," *N. Engl. J. Med.*, vol. 344, 2001, pp.: 873–880.

Chamorro, JL, et. al., "Ejection VAVE; EF and Phase Histogram to Evaluate a Correct Programation of AV Delay in DDD Pacemakers," *European Journal of Nuclear Medicine*, vol. 8, No. 5, 1983, Abstract P96.

Chamorro, JL, et. al., "Quantification of Experimental Myocardial Infarction with 99TcGlucogeptonate," *European Journal of Nuclear Medicine*, vol. 8, No. 5, 1983, Abstract P104.

D'Ajutolo, R, and Posse, R, Tratamiento de Las Arritmias Cardiacas, Buenos Aires 1968 and English–language translaton of Chapter 10.

De Teresa, E., Grandes Temas de la Medicina: Marcapasos, Nueva Lente, Madrid 1987.

De Teresa, et al., "Haemodynamics of Ventricular Depolarization Sequence During Permanent Cardiac Pacing," *Cardio Stimolazione*, vol. 2, No. 3, 1984, p. 225.

Diotallevi, P, et al., "Rescuing Failed Biventricular Implants Using Right Ventricular Bifocal Pacing to Assure Cardiac Resynchronization Benefits to Heart Failure Patients," Heart Rhythm, vol. 3, No. 5, May Supplement 2006, Abstract No. AB48–2.

Dreifus, L, et al., "Effects of AV Sequential Versus Asynchronous AV Pacing on Pulmonary Hemodynamics," *PACE*, vol. 9, No. 2, Mar.–Apr. 1986, pp. 171–177.

Ellenbogen KA, et al., Clinical Cardiac Pacing and Defibrillation, 2nd Edition, Philadelphia, W.B. Saunders Co., 2000.

Elmqvist, R, et al., "An Implantable Pacemaker for the Heart," Medical Electronics: Proceedings of the Second International Conference on Medical Electronics, Smyth, CN, ed., Jun. 1959, London, UK, Iliffe & Sons; pp. 253–254.

Escher, DJW, "Historical Aspects of Cardiac Pacing," Cardiac Pacing (2nd Ed.), Samet, P, et al., eds., New York, Grune & Stratton, 1979, pp. 631–643.
Etienne, Y, et al., "Evaluation of Left Ventricular Based Pacing in Patients With Congestive Heart Failure and Atrial Fibrillation," *Am. J. Cardiol.*, vol. 83, 1999, pp. 1138–1140.
Fields, J, et al., "Surgical Experience With Temporary and Permanent A–V Sequential Demand Pacing," *J. of Thoracic and Cardiovascular Surgery*, vol. 66, No. 6, Dec. 1973, pp. 865–877.
Fletcher, FW, et al., "Effect of Pacemaker Location on Cardiac Function in Complete Heart Block," *Am. J. Physiol.*, 1963; 205:1232–34.
Gabrielle, O. F., "Pacing Via Coronary Sinus," *N. Engl. J. Med.*, vol. 280, No. 4, 1969, p. 219.
Greenberg, et al., "Coronary Sinus Pacing: Clinical Follow–up," *Circulation*, vol. 57, No. 1, Jan. 1978, pp. 98–103.
Hayes, D., "Pacemakers" in Comprehensive Cardiovascular Medicine, EJ Topol, ed., Philadelphia, Lippincott–Raven Publishers, 1998, pp. 2099–2132.
Higgins SL, et al. "Cardiac Resynchronization Therapy for the Treatment of Heart Failure in patients With Intraventricular Conduction Delay and Malignant Ventricular Tachyarrhythmias," *J. Am. Coll. Cardiol.*, Vo. 42, No. 8, 2003, pp. 1454–1459.
Holmes, DR, et al., "Pacemaker Implantation Techniques," in Electrical Therapy for Cardiac Arrhythmias, Saksena, S, et al., eds., Philadelphia, WB Saunders Co., 1990, pp. 173–190.
Kass DA, et al., "Improved Left Ventricular mechanics From Acute VDD Pacing in Patients With Dilated Cardiomyopathy and Ventricular Conduction Delay," *Circulation*, vol. 99, No. 12, Mar. 1999, pp. 1567–1573.
Kastor, J, et al., "Variations in Discharge Rate of Demand Pacemakers Not Due to Malfunction," *Am. J. of Cardiology*, vol. 25, No. 3, Mar. 1970, pp. 344–348.
Keller, J. Walter, "Atrial and Ventricular Syncrhony: The Engineering–Physiology Interface," *Annals of the New York Academy of Sciences*, vol. 167, 1969, pp. 869–885.
Kramer, D. H et al., "Permanent Pervenous Atrial Pacing from the Coronary Vein," *Circulation*, vol. 42, 1970, pp. 427–436.
Leclercq C, et al., "Acute Hemodynamic Effects of Biventricular DDD Pacing in Patients With End–Stage Heart Failure," *J. Am. Coll. Cardiol.*, vol. 32, No. 7, Dec. 1998, pp. 1825–1831.
Leclercq C, et al., "Triple Site Ventricular Pacing for Optimizing Ventricular Resynchronization: Design of the Trip–HF Study; Technical Feasibility," Heart Rhythm, vol. 3, No. 5, May Supplement 2006, Abstract No. AB48–3.
Lemberg, L, et al., "Demand and Bifocal Demand Pacing," *Singapore Med. J.*, vol. 14, No. 3, Sep. 1973, pp. 222.
Lemberg, L, et al., "Pacemaking on Demand in AV Block," *JAMA*, vol. 191, No. 1, Jan. 1965, pp. 106–108.
Lemberg, L, et al., "Systolic and Diastolic Pacemaker Induced Repetitive Firing in the Human Heart: Analysis of 23 Cases," *J. Electrocardiology*, vol. 2 No. 4, Oct. 1969, pp. 353–362.
Lown, B, et al., "Comparison of Alternating Current with Direct Current Electroshock Across the Closed Chest," *Am. J. of Cardiology*, Aug. 1962, pp. 223–233.
Lurie KL, et al., "Development of Multifunctional Coronary Sinus Catheter," *RBM* (*Revue Europeenne Technologie Biomedicale*) 1994, 16:159–61.
Mansouratii J, et al., "Left Ventricular–based Pacing in Patients With Chronic Heart Failure: Comparison of Acute Hemodynamic Benefits According to Underlying Heart Disease," *European Journal of Heart Failure*, 2 (2000):195–99.
Maytin, O, et al., "Diagramatic Representation of Pacemaker Arrhythmias," *J. Electrocardiology*, vol. 3, No. 3–4, 1970, pp. 251–257.
Medina–Ravell, V, et al., "Management of Tachyarrhythmias With Dual–Chamber Pacemakers," *PACE*, vol. 6, No. 2, Mar.–Apr. 1983, Part II, pp. 333–345.
Medina–Ravell, V, et al., "Use of Dual–Demand AV Sequential (DVI, MN) Pacemakers in the Management of Supraventricular Tachycardias," *Pacemaker Therapy*, L. Dreifus ed., 1983, pp. 227–238.
Medtronic Model 5330 A–V Sequential Demand Pulse Generator, Technical Manual, Jun. 1978.
Miyazawa, K, et al., "Effects of Varying Pacemaker Sites on Left Ventricular Performance," *Tohoku J. exp. Med.*, 1976, 120, pp. 301–308.
Miyazawa, K, et al., "Regional Contraction Patterns of the Left Ventricle during Ventricular Pacing," *Tohoku J. exp. Med.* 1977, 122; pp. 167–174.
Moss, AJ et al., "Atrial Pacing from the Coronary Vein: Ten–Year Experience in 50 Patients with Implanted Pervenous Pacemakers," *Circulation*, vol. 57, No. 1, 1978, pp. 103–106.
Nelson, GS, et al. "Left Ventricular or Biventricular Pacing Improves Cardiac Function at Diminished Energy Cost in Patients With Dilated Cardiomyopathy and Left Bundle–Branch Block," *Circulation*, vol. 102, 2000, pp. 3053–3059.
Niazi, I. et al., "Dual–Site Left Ventricular Stimulation Provides Better Resynchronization Response than Conventional Biventricular Stimulation," Heart Rhythm, vol. 3, No. 5, May Supplement 2006, Abstract No. AB42–6.
Obel, IWP, Physiological Pacing, Pitman Medical, London, 1979.
Ogawa, S, et al., "Hemodynamic Consequences of Atrioventricular and Ventriculoatrial Pacing," *PACE*, vol. 1, No. 1, Jan.–Apr. 1978, pp. 8–15.
Popovic ZB, et al., "Noninvasive Assessment of Cardiac Resynchronization Therapy for Congestive Heart Failure Using Myocardial Strain and Left Ventricular Peak Power as Parameters of Myocardial Synchrony and Function," *J. Cardiovasc Electrophys.*, vol. 13, No. 12, 2002, pp. 1203–1208.
Portillo, B, et al., "Treatment of Drug Resistant A–V Reciprocating Tachycardias With Multiprogrammable Dual Demand A–V Sequential (DVI, MN) Pacemakers," *PACE*, vol. 5, No. 6, 1982, pp. 814–825.
Prauer, H, et al., "Prolonged Electrostimulaton of the Heart Through the Coronary Sinus; Report of Two Cases with Position of the Electrode Confirmed by Autopsy," *Thoraxchirugie Vaskulare Chirurgie*, 1974, 22, p. 207.
Program of the VIIth World Symposium on Cardiac Pacing, Vienna, May 1–5, 1983, in *Schrittmacher: German Journal of Cardiac Pacing*, Apr. 1983, listing De Teresa et al., "An Even More Physiological Pacing Changing the Sequence of Ventricular Activation."
Rodriguez Bailon, I, et al., "Some Data for an Unanswered Question: Choosing the Ventricular Electrode Place," *PACE*, vol. 8, No. .3 Part II, May 1985, p. A–11.

Rogel, S, et al., "Atrioventricular Time Sequence and Myocardial Efficiency," *Archives Internationales de Physiologie et de Biochimie*, 1973, 81, 833–42.
Romero, L., et al., "Non–Invasive Evaluation of Ventricular Function and Volumes During Atrioventricular Sequential and Ventricular Pacing," *PACE*, vol. 7, No. 1, Jan. 1984, pp. 10–17.
Royal Decree 185/1985, Jan. 23, 1985, Spanish Ministry for Education and Science (Certified English translation and Spanish original).
Royal Decree Amendments 185/195.
Silva, "Influencia de la Localizacion de la Estimulacion Electrica Ventricular Sobre la Eficiencia Cardiaca. Estudio Experimental Y Clinico," ["Influence of the Location of the Location of Ventricular Electrical Stimulaton on Cardiac Efficiency"], Tesis Doctoral para la Universidad Autonoma De Madrid Facultad de Medicina (Dated 1987) (Spanish with English–Language Translation Attached).
Silva et al., "Biventricular Stimulation: An Approach to Physiologic Cardiac Stimulation," *International Congress of Cardiology*, 1988, p. 132.
Silva et al., "Biventricular Stimulation: A More Physiologic Pacing," *4th European Symposium on Cardiac Pacing, Abstract Book*, May 31, 1989, p. 148, Abstract 339.
Program of *International Congress of Cardiology*, Marrakesh, Morocco, Nov. 1988, listing Silva et al, "Biventricular Stimulation: An Approach to Physiologic Cardiac Stimulation."
International Congress of Cardiology Program, Friday, Nov. 4, 1988, listing Silva et al., "Biventricular Stimulation: An Approach to Physiologic Cardiac Stimulation."
Silva et al., "Epicardial Biventricular Stimulation Mimicking Activation During Sinus Rhythm. Experimental Study" *European Heart Journal*, vol. 8, Supp. 2, Sep. 1987, p. 180.
Smyth et al., "Permanent Pervenous Atrial AV Synchronous and AV Sequential Pacing," Cardiac Pacing, Thalen, H, ed., Van Gorcum: Assen, Netherlands, 1973, p. 145.
Stokes, K, et al., "The Electrode–Biointerface–Stimulation," Modern Cardiac Pacing, Barold, SS, ed., Futura Publishing, 1985, pp. 33–78.
Sutton, R, et al., "The History of Cardiac Pacing," The Foundations of Cardiac Pacing, Futura Publishing, Mt. Kisco, NY, 1991, pp. 319–324.
Yoshida, K., et al., "Tripolar–Ventricular Pacing Improves Both Systolic and Diastolic Left Ventricular Function in Patients with End–Stage Heart Failure," Heart Rhythm, vol. 3, No. 5, May Supplement 2006, Abstract No. P6–96.
Young JB, et al; "Combined Cardiac Resynchronization and Implantable Cardioversion Defibrillation in Advanced Chronic Heart Failure: The Miracle ICD Trial," *JAMA*, vol. 238, No. 20, pp. 2685–2694.
Zaroff, L, et al., "An Implantable Demand Pacemaker," *The Annals of Thoracic Surgery*, vol. 4, No. 5, Nov. 1967, pp. 463–467.
Zoll, P, "Resuscitation of the Heart in Ventricular Standstill by External Electrical Stimulation," *N. Engl J. Med.*, vol. 247, No. 20, 1952, pp. 768–771.
Zuckerman, W, et al., "Clinical Applications of Demand Pacing," *Annals of the New York Academy of Sciences*, vol. 167, No. 2, Oct. 30, 1969, pp. 1055–1059.
Zuckerman, W, et al., "Clinical Experiences With a New Implantable Demand Pacemaker," *Am. J. of Cardiology*, vol. 20, Aug. 1967, pp. 232–238.
Updated Case Docket for *Medtronic, Inc.* v. *Guidant Corp.*, No. 03–848–SLR (D. Del.).
Order dated Jul. 19, 2005 that RE38,119 is not invalid, issued in *Medtronic, Inc.* v. *Guidant Corp.*, No. 03–848–SLR (D. Del.).
Opinion accompanying Order dated Jul. 19, 2005, issued in *Medtronic, Inc.* v. *Guidant Corp.*, No. 03–848–SLR (D. Del.).
Initial Expert Report of Janice M. Jenkins, PhD, (Expert for Medtronic, Inc.) from *Medtronic, Inc.* v. *Guidant Corp.*, No. 03–848–SLR (D. Del.) (With Accompanying Exhibits 1–37).
Supplemental Expert Report of Janice M. Jenkins, PhD, (Expert for Medtronic, Inc.) from *Medtronic, Inc.* v. *Guidant Corp.*, No. 03–848–SLR (D. Del.) (With Accompanying Exhibits 38–46).
Transcript of the Deposition of Janice M. Jenkins, Ph.D., taken Sep. 23, 2004 in *Medtronic, Inc.* v. *Guidant Corp.*, No. 03–848–SLR (D. Del.).
Transcript of the Deposition of Edward V. Platia, M.D., taken Aug. 31, 2004 in *Medtronic, Inc.* v. *Guidant Corp.*, No. 03–848–SLR (D. Del.).
Transcript of the Deposition of H. Troy Nagle, Ph.D., M.D., taken Aug. 6, 2004 in *Medtronic, Inc.* v. *Guidant Corp.*, No. 03–848–SLR (D. Del.).
Transcript of the Deposition of Morton M. Mower, M.D., taken Apr. 22, 2004 in *Medtronic, Inc.* v. *Guidant Corp.*, No. 03–848–SLR (D. Del.).
Trial Transcript, vol. A (Nov. 1, 2004) from *Medtronic, Inc.* v. *Guidant Corp.*, No. 03–848–SLR (D. Del.).
Trial Transcript, vol. B (Nov. 2, 2004) from *Medtronic, Inc.* v. *Guidant Corp.*, No. 03–848–SLR (D. Del.).
Trial Transcript, vol. C (Nov. 3, 2004) from *Medtronic, Inc.* v. *Guidant Corp.*, No. 03–848–SLR (D. Del.).
Updated Case Docket for *Guidant Corp.* v. *St. Jude Medical, Inc.*, No. 04–0067–SLR (D. Del.).
Defendants' (St. Jude et al.) Motion for Summary Judgment of Invalidity Based on Reissue Recapture from *Guidant Corp.* v. *St. Jude Medical, Inc.*, No. 04–0067–SLR (D. Del.).
Plaintiffs' (Guidant et al.) Opposition to Defendants' (St. Jude et al.) Motion for Summary, Judgment of Invalidity Based on Reissue Recapture from *Guidant Corp.* v. *St. Jude Medical, Inc.*, No. 04–0067–SLR (D. Del.).
Defendants' (St. Jude et al.) Reply in Support of Their Motion for Summary Judgment of Invalidity Based on Reissue Recapture from *Guidant Corp.* v. *St. Jude Medical, Inc.*, No. 04–0067–SLR (D. Del.).
Second Amended Complaint from *Guidant Corp.* v. *St. Jude Medical, Inc.*, No. 04–0067–SLR (D. Del.).
Answer to Second Amended Complaint and Counterclaims from *Guidant Corp.* v. *St. Jude Medical, Inc.*, No. 04–0067–SLR (D. Del.).
Plaintiffs' (Guidant et al.) Responses to Defendants' (St. Jude et al.) First and Second Sets of Interrogatories (1–17) from *Guidant Corp* v. *St. Jude Medical, Inc.*, No. 04–0067–SLR (D. Del.).
Plaintiffs' (Guidant et al.) Responses to Defendants' (St. Jude et al.) Third Set of Interrogatories (18–35) from *Guidant Corp* v. *St. Jude Medical, Inc.*, No. 04–0067–SLR (D. Del.).
Plaintiffs' (Guidant et al.) Supplemental Responses to Defendants' (St. Jude et al.) First and Second Sets of Interrogatories (1–17) from *Guidant Corp.* v. *St. Jude Medical, Inc.*, No. 04–0067–SLR (D. Del.).

Plaintiffs' (Guidant et al.) Responses to Defendants' (St. Jude et al.) First Set of Requests for Admissions (1–26) from *Guidant Corp.* v. *St. Jude Medical, Inc.*, No. 04–0067–SLR (D. Del.).

Defendants' (St. Jude et al.) Responses to Plaintiffs' (Guidant et al.) Fourth Set of Interrogatories (19–20) from *Guidant Corp.* v. *St. Jude Medical, Inc.*, No. 04–0067–SLR (D. Del.).

Defendants' (St. Jude et al.) Supplemental Responses to Plaintiffs' (Guidant et al.) First Set of Interrogatories (2 & 9) from *Guidant Corp.* v. *St. Jude Medical, Inc.*, No. 04–0067–SLR (D. Del.).

Defendants' (St. Jude et al.) Responses to Plaintiffs' (Guidant et al.) First Set of Requests for Admissions (1–34) from *Guidant Corp.* v. *St. Jude Medical, Inc.*, No. 04–0067–SLR (D. Del.).

Letter from M. Mower, M.D. to Sinai Hospital of Baltimore dated May 30, 1988.

Letter from M. Mower, M.D. to Sinai Hospital of Baltimore dated Jun. 24, 1988.

Document entitled "Pertinent Bibliography".

Biography of Barouh V. Berkovits.

Benchimol et al., "Contribution of Atrial Systole to the Cardiac Function at a Fixed and at a Variable Ventricular Rate," *The American Journal of Cardiology*, vol. 16, No. 1, Jul. 1965, pp. 11–21.

De Teresa, et al., "Haemodynamics of Ventricular Depolarization Sequence During Permanent Cardiac Pacing," *Progress in Clinical Pacing*, Publication Date Unknown.

Magder et al., "Effect of Negative Pleural Pressure on Left Ventricular Hemodynamics," *Am. J. of Cardiology*, Sep. 1, 1983 52(5), pp. 588–593 (Abstract Only).

Samet et al., "Electrical Activation and Mechanical Asynchronism in the Cardiac Cycle of the Dog," *Circulation Research*, vol. VII, Mar. 1959, pp. 228–233.

Walsh et al., "Differentiation of Sinus Rhythms for Supraventricular Tachydysrhythmias by Activation Sequence and Timing," *PACE* Dec. 1990;13(12 Pt2): 1972–9 (Abstract Only).

Lima et al., "Incomplete Filling and Incoordinate Contraction as Mechanisms of Hypotension during Ventricular Tachycardia in Man," Circulation, vol. 68, No. 5, pp. 928–937 (1983).

Aranda, et al., "A New Pacemaker for Simultaneous Biventricular Stimulation of the Human Heart," Clin. Res., vol. XXIV, No. 3, p. 206A (1976).

Befeler et al., "Programmed Simultaneous Biventricular Stimulation in Man, with Special Reference to its Use in the Evaluation of Intraventricular Reentry," Eur. J. of Cardiology, vol. 9, No. 5, pp. 369–378 (1979).

Haas et al., "Pacemaker–Induced Cardiovascular Failure," Am. J. of Cardiology, vol. 33, pp. 295–299 (1974).

Lister et al., "Effect of Pacemaker Site on Cardiac Output and Ventricular Activation in Dogs with Complete Heart Block," Am. J. of Cardiology, vol. 14, pp. 494–503 (1964).

Mann et al., "Importance of Pacing Site in Entrainment of Ventricular Tachycardia," J. Am. College of Cardiology, vol. 5, No. 3, pp. 781–787 (1985).

Schlant et al., "Modification of the Law of the Heart: Influence of Early Contracting Areas (P)," Supp. to Circulation, vols. XXIX and XXX, pp. III –153, 154 (1964).

Tyers, G., "Comparison of the Effect on Cardiac Function of Single–Site and Simultaneous Multiple–Site Ventricular Stimulation After A–V Block," J. Thoracic and Cardiovas. Sur., vol. 59, No. 2, pp. 211–217 (1970).

William–Olsson et al., "The Effect of Pacemaker Electrode Site on Cardiac Output," J. Thoracic and Cardivas. Surg., vol. 45, No. 5, pp. 618–621 (1963).

Zile et al., "Right Ventricular Pacing Reduces the Rate of Left Ventricular Relaxation and Filling," J. Am. Coll. Cardiol., vol. 10, No. 3, pp. 702–709 (1987).

Case Docket for *Medtronic, Inc.* v. *Guidant Corp.*, No. 1:03–CV–0742 (S.D. Ind.).

Complaint for Declaratory Judgment, filed in *Medtronic, Inc.* v. *Guidant Corp.*, No. 1:03–CV–0742 (S.D. Ind.).

Order Granting Motion for Stay, issued in *Medtronic, Inc.* v. *Guidant Corp.*, No. 1:03–CV–0742 (S.D. Ind.).

Order Lifting Stay and Dismissing Action Without Prejudice, issued in *Medtronic, Inc.* v. *Guidant Corp.*, No. 1:03–CV–0742 (S.D. Ind.).

Case Docket for *Medtronic, Inc.* v. *Guidant Corp.*, No. 03–848 (D. Del.).

First Amended Complaint for Declaratory Judgment, filed in *Medtronic, Inc.* v. *Guidant Corp.*, No. 03–848 (D. Del.).

Plaintiff's Responses to Defendants' Interrogatories 1–4, filed in *Medtronic, Inc.* v. *Guidant Corp.*, No. 03–848 (D. Del.).

First Amended Answer, filed in *Medtronic, Inc.* v. *Guidant Corp.*, No. 03–848 (D. Del.).

Case Docket for *Guidant Corp.* v. *St. Jude Medical, Inc.*, No. 04–0067 (D. Del.).

Complaint, filed in *Guidant Corp.* v. *St. Jude Medical, Inc.*, No. 04–0067 (D. Del.).

Case Docket for *Medtronic, Inc.* v. *Guidant Corp.*, No. 1:03–CV–0743 (S.D. Ind.).

Complaint for Declaratory Judgment, filed in *Medtronic, Inc.* v. *Guidant Corp.*, No. 1:03–CV–0743 (S.D. Ind.).

Notice of Voluntary Dismissal, filed in *Medtronic, Inc.* v. *Guidant Corp.*, No. 1:03–CV–0743 (S.D. Ind.).

Case Docket for *St. Jude Medical, Inc.* v. *Guidant Corp.*, No. 1:04–CV–0447 (S.D. Ind.).

Complaint for Declaratory Relief, filed in *St. Jude Medical, Inc.* v. *Guidant Corp.*, No. 1:04–CV–0447 (S.D. Ind.).

Notice of Dismissal, filed in *St. Jude Medical, Inc.* v. *Guidant Corp.*, No. 1:04–CV–0447 (S.D. Ind.).

Updated Case Docket for *Medtronic, Inc.* v. *Guidant Corp.*, No. 03–848–SLR (D. Del.).

Memorandum Order Dated Apr. 21, 2004, issued in *Medtronic, Inc.* v. *Guidant Corp.*, No. 03–848–SLR (D. Del.).

Order Dated Jul. 8, 2004, issued in *Medtronic, Inc.* v. *Guidant Corp.*, No. 03–848–SLR (D. Del.).

Order Dated Oct. 6, 2004, issued in *Medtronic, Inc.* v. *Guidant Corp.*, No. 03–848–SLR (D. Del.).

Order Dated Oct. 25, 2004, issued in *Medtronic, Inc.* v. *Guidant Corp.*, No. 03–848–SLr (D. Del.).

Initial Expert Report of Janice M. Jenkins, PhD, (Expert for Medtronic, Inc.) from *Medtronic, Inc.* v. *Guidant Corp.*, No. 03–848–SLR (D. Del.).

Supplemental Expert Report of Janice M. Jenkins, PhD, (Expert for Medtronic, Inc.) from *Medtronic, Inc.* v. *Guidant Corp.*, No. 03–848–SLR (D. Del.).

Expert Report of Edward V. Platia, MD, FACC (Expert for Guidant, et al.) from *Medtronic, Inc.* v. *Guidant Corp.*, No. 03–848–SLR (D. Del.).

Supplemental Expert Report of Edward V. Platia, MD, FACC (Expert for Guidant, et al.) from *Medtronic, Inc.* v. *Guidant Corp.*, No. 03–848–SLR (D. Del.).

Expert Report of H. Troy Nagle, PhD, MD (Expert for Guidant, et al.) from *Medtronic, Inc.* v. *Guidant Corp.*, No. 03–848–SLR (D. Del.).

Medtronic's Corrected Opening Post–Trial Memorandum (Dated Feb. 7, 2005) from *Medtronic, Inc.* v. *Guidant Corp.*, No. 03–848–SLR (D. Del.).

Medtronic's Second Corrected Post–Trial Reply Brief (Dated Feb. 28, 2005) from *Medtronic, Inc.* v. *Guidant Corp.*, No. 03–848–SLR (D. Del.).

Updated Case Docket for *Guidant Corp.* v. *St. Jude Medical, Inc.*, No. 04–0067–SLR (D. Del.).

First Amended Complaint, filed in *Guidant Corp.* v. *St. Jude Medical, Inc.*, No. 04–0067–SLR (D. Del.).

Answer to First Amended Complaint and Counterclaims, filed in *Guidant Corp.* v. *St. Jude Medical, Inc.*, No. 04–0067–SLR (D. Del.).

Plaintiffs' Reply to Defendants' Counterclaims, filed in *Guidant Corp.* v. *St. Jude Medical, Inc.*, No. 04–0067–SLR (D. Del.).

Defendants' (St. Jude Medical et al.) Brief in Support of Their Motion for Leave to File an Early Summary Judgment Motion on a Single Issue (Dated Jan. 5, 2005) from *Guidant Corp.* v. *St. Jude Medical, Inc.*, No. 04–0067–SLR (D. Del.).

Plaintiffs' (Guidant et al.) Opposition to Defendants' Motion for Leave to File an Early Summary Judgment Motion (Dated Jan. 20, 2005) from *Guidant Corp.* v. *St. Jude Medical, Inc.*, No. 04–0067–SLR (D. Del.).

Defendants' (St. Jude Medical et al.) Reply in Support of Their Motion for Leave to File an Early Summary Judgment Motion on a Single Issue (Dated Jan. 27, 2005) from *Guidant Corp.* v. *St. Jude Medical, Inc.*, No. 04–0067–SLR (D. Del.).

Defendants' (St. Jude Medical et al.) Responses to Plaintiffs' First Set of Interrogatories from *Guidant Corp.* v. *St. Jude Medical, Inc.*, No. 04–0067–SLR (D. Del.).

American Optical Corp., Biventricular Pacer Device, 1975.

Badeer, HS, "Relation of ECG to Mechanical Events," *Cardiovascular Physiology*, 1984, 6:57–58.

Bakker et al., "Beneficial Effects of Biventricular Pacing in Congestive Heart Failure," *PACE*, Apr. 1994,17 (4):820.

Bakker et al., "Biventricular Pacing in Congestive Heart Failure," *Clinical Research*, Apr. 1994, vol. 42, No. 2.

Bakker et al., "Biventricular Pacing Improves Functional Capacity in Patients with End–Stage Congestive Heart Failure," *PACE*, 1995 (18):825.

Barold et al., "First Reports of Electrical Multisite Ventricular Activation in Humans," *PACE*, Dec. 2000, (23):2117–2119.

Bashir et al., "Combined Use of Transesophageal ECHO and Fluoroscopy For the Placement of Left Ventricular Pacing Leads Via the Coronary Sinus," *PACE*, Oct. 2003, (26):1951–1954.

Benchimol et al., "Cardiac Hemodynamics During Stimulation of the Right Atrium, Right Ventricle, and Left Ventricle in Normal and Abnormal Hearts," *Circulation*, Jun. 1996, (38).

Blackburn et al., "Ventricular Pacing from the Coronary Sinus of a Patient with a Fontan Circulation," *Br. Heart J.*, 1993, (70):578–579.

Bocchiardo et al., "Efficacy of Biventricular Sensing and Treatment of Ventricular Arrhythmias," *PACE*, Nov. 2000, 1989–1991.

Bourassa, M, "Hemodynamic Studies During Intermittent Left Bundle Branch Block," *American Journal of Cardiology*, Dec. 1962, 792–799.

Bove AA, et al., "Ventricular Interdependence," *Prog Cardiovasc Dis.*, Mar.–Apr.1981; 23(5):365–388.

Bracke et al., "Extraction of Pacemaker and Implantable Cardioverter Defibrillator Leads: Patient and Lead Characteristics in Relation to the Requirement of Extraction Tools," *PACE*, Jul. 2002, (25):1037–1040.

Broka, S, "Hemodynamic Effects of Atrio–Biventricular Pacing," *Ann. Thoracic Surg.*, 1995, (60):1156.

Brownlee RR, et al., "New Functional Configurations for Adaptive Pacemakers," 28$^{th}$ ACEMB, New Orleans, Sep. 20–24, 1975, p. 84.

Brownlee RR, et al., "Advances in ventricular synchronous demand cardiac pacemakers," *Med Instrum*, Mar.–Apr. 1978; 12(2):94–99.

Brownlee RR, et al., "New Interference Sensing Demand Pacemaker Functions," *IE Transaction on Biomedical Engineering*, May 1978, vol. BME 25, No. 3.

Castellanos, A, "Bipolar Coronary Sinus Lead For Left Atrial and Left Ventricular Recording," *American Heart Journal*, 1971, vol. 81, No. 6, 832–836.

Castellanos, A, "Measurement of Conduction Times With Catheter Electrodes During Pacing From Different Ventricular Sites," *British Heart Journal*, 1975, (37):242–248.

Castellanos et al., "Unusual QRS Complexes Produced by Pacemaker Stimuli," *American Heart Journal*, Jun. 1969, vol. 77, No. 6, 732–742.

Cazeau et al., "Four Chamber Pacing in Dilated Cardiomyopathy," *PACE*, Nov. 1994, Part II, vol. 17, 1974–1979.

Cazeau et al., "Multisite Pacing for End–Stage Heart Failure," *PACE*, Nov. 1996, (19):1748–1757.

Cazeau et al., "Echocardiographic Modeling of Cardiac Dyssynchorny Before and During Multisite Stimulation: A Prospective Study," *PACE*, Jan. 2003, Part II, vol. 26, 137–143.

Cohen et al., "Hemodynamic Responses to Rapid Pacing: A Model for Tachycardia Differentiation," *PACE*, Nov. 1988, (11):1522–1528.

Cordis Manual, "Atricor, Implantable P–Wave Synchronized," Model 145, 149–Rev. 3A, Oct. 1973.

Curtiss EI, et al., "Electrocardiographically Discrete Right and Left Ventricular QRS Complexes: A Case Report," *J. Electrocardiol*, Apr. 1987; 20(2):162–168.

Dawson, Jr, et al., "Regional left ventricular wall motion in pacing induced angina," *Br. Heart J.* Mar. 1988; 59(3):309–318.

Dawson, Jr, et al., "Left ventricular filling and early diastolic function at rest and during angina in patients with coronary artery disease," *Br. Heart J.* Mar. 1989, 61(3):248–257.

De Teresa et al., "An Even More Physiological Pacing: Changing the Sequene of Ventricular Activation," 395–400 [no information regarding publisher].

Dreifus LS, et al., "Use of atrial and bifocal cardiac pacemakers for treating resistant dysrhythmias," *Eur J Cardiol*, Dec. 1975; 3(4): 257–266.

Dreifus LS, et al., "Effect of multiple simultaneous activation sites (biventricular pacing) on ventricular depolarization and ventricular arrhythmias," *Cardiac Pacing, Proceedings of the Vth International Symposium, Tokyo*, Mar. 1976, 33–39.

Duck HJ, et al., "Vorhofsynchrone Ventrikelstimulation mit verkürzter a.v. Verzögerungszeit als Therapieprinzip der hypertrophischen obstruktiven Kardiomyopathie" "[Atrial Synchronous Ventricular Stimulation With Reduced a.v. Delay Time as a Therapeutic Principle In Hypertrophic Obstructive Cardiomyopathy]," *Z. Gesamte Inn Med*, Sep. 15, 1984, (39):18 437–447. (German with English–Language Abstract Attached).

Erdogan et al., "Proportion of Candidates for Cardiac Resynchronization Therapy," *PACE*, Jan. 2003, Part II, 26:152–154.

Fei et al., "Effects of Multisite Ventricular Pacing on Cardiac Function in Normal Dogs and Dogs with Heart Failure," *Journal of Cardiovascular Electrophysiology*, Jul. 1999, 10(7): 935–944.

Finney, JO, "Hemodynamic Alterations in Left Ventricular Function Consequent to Ventricular Pacing," *American J. Physiology*, 1965, (208):275–282.

Foster, A, "Acute Hemodynamic Effects of Atrio–Biventricular Pacing in Humans," *Annals of Thoracic Surg.*, 1995, 294–300.

Funke HD, "[Optimized Sequential Pacing of Atria and Ventricles—A New Concept in the Treatment of Bradycardial Dyshrythmias]," *Univ Clinic for Cardiac and Vascular Surg Bonn, Herz/Kreisl*. 1978; 10(10):479–483 (German with English–Language Abstract and English Translation Attached).

Furuta, T, "[Assessment of interaction between the left and right ventricles using pressure–volume loops in various heart diseases], " J. Cardiol. Jun. 1988; 18(2):477–491. (Japanese with English Abstract and Figure Captions).

Gasparini et al., on behalf of the Italian InSync ICD Registry Investigators, "Cardiac Resynchronization and Implantable Cardioverter Defibrillator Therapy: Preliminary Results from the InSync Implantable Cardioverter Defibrillator Therapy," *PACE*, Jan. 2003, 26(1):2, 148–151.

Gasparini et al., "Beneficial Effects of Biventricular Pacing in Patients with a 'Narrow' QRS," *PACE*, Jan. 2003, 26(1):2, 169–174.

Gibson DG, et al., "Effect of Changes in Ventricular Activation on Cardiac Hemodynamics in Man, Comparison of Right Ventricular, Left Ventricular, and Simultaneous Pacing of Both Ventricles," *Br Heart J.*, May 1971; 33:397–400.

Gilmore JP, et al., "Synchronicity of Ventricular Contraction: Observations Comparing Hemodynamic Effects of Atrial and Ventricular Pacing," *Br Heart J.*, May 1963; 25:299–307.

Greatbatch, W, "The Making of the Pacemaker: Celebrating Lifesaving Invention," *Prometheus Books*, 2000.

Greatbatch, W. *Pacemaker*. 2000: 14–19.

Gomez–Doblas et al., "Ventricular Geometry And Heart Failure," *Rev Esp Cardiol.*, Jan. 1999: 52(1):47–52. Review. (Spanish with English Abstract).

Grover et al., "Endocardial Pacing Site Affects Left Ventricular End–Diastolic Volume and Performance in the Intact Anesthetized Dog," *Circulation Research*, Jul. 1983, 53(1).

Hauser et al., "Performance of Pacemaker and Implantable Cardioverter Defibrillator Pulse Generators and Leads: Results from the Multicenter Registry," *The XI World Congress on Cardiac Pacing & Electrophysiology, Hong Kong*, Feb. 19–20, 2003, 173–179.

Hayes et al., "Cardiac Pacing: How it Started, Where We Are, Where We Are Going," *PACE*, May 2004, 27:693–704.

Hochleitner et al., "Usefulness of Physiologic Dual–chamber Pacing in Drug–Resistant Idiopathic Dilated Cardiomyopathy," *American Journal of Cardiology*, Jul. 15, 1990, (66):198–202.

Hughes et al., "Effect of Stimulation Site on Ventricular Threshold in Dogs with Heart Block," *American Heart Journal* (*Am. Heart J.*) 1975, 89/1 (pp. 68–73).

Hughes et al., "Two To Three Years of Failure Free Testing of a Rechargeable Pacemaker in Experimental Complete Heart Block," *Circulation* 1976, 54/2 (pp. 263–266).

Hughes et al., "The Effects Of Electrode Position On The Detection Of The Transvenous Cardiac Electrogram," *PACE*, 1980, 3(6):651–655.

Hunt et al., "Long–term Electrode Catheter Pacing from Coronary Sinus," *Medical Memoranda, British Medical Journal*, Nov. 23, 1968, 495–496.

Janosik et al., "The Hemodynamic Benefit of Differential Atrioventricular Delay Intervals for Sensed and Paced Atrial Events During Physiologic Pacing," *J Am Coll Cardiol*, Aug. 1989 14:2, 499–507.

Jeffrey, K, Excerpts from *Machines in Our Hearts*, 2001.

Jimenez–Navarro et al., Correspondence to the Editor about "Left Ventricular Assist Device," *N Engl J Med.*, Mar. 28, 2002, 346(13): 1023–1025; author reply 1023–1025.

Karlöf, Ingvar, "Haemodynamic Effect of Atrial Triggered Versus Fixed Rate Pacing at Rest and During Exercise in Complete Heart Block," *Acta Med Scand*, 197(3):195–206, Mar. 1975.

Kawamura et al. "[Experimental Study of RV–LV Simultaneous Pacing As More Physiological Pacing]," Shintaro Shibata Cardiac Research Laboratory, Internal Medicine, Tokyo Women's Medical University, 1982, 285–286. (Japanese with English Translation).

Kennergren et al., "Cardiac Lead Extraction with a Novel Locking Stylet" *Journal Of Interventional Cardiac Electrophysiology*, 2000, V4, n4 (DEC), P591–593.

Kerr et al., "Transvenous Atrial Pacing Following Amputation of the Atrial Appendage at Open Heart Surgery," *PACE*, Jul.–Aug. 1985, (8):497–501.

Kerr et al., "Atrial Pacing: Efficacy and Safety," *PACE*, Jul. 1989 12(1):1049–1054.

Klug et al., "Pacemaker Lead Extraction With the Needle's Eye Snare for Countertraction Via a Femoral Approach," *PACE*, Jul. 2002, 25(7), 1023–1028.

Lattuca et al., "Bi–Ventricular Pacing to Improve Cardiac Hemodynamics," *Clinical Research*, Oct. 1990, 38 (3):882A.

Marchlinski et al., "Atrial and Ventricular Burst Pacing from a Coronary Sinus Catheter: Relation to Position of Radiofrequency Transmitter," *PACE*, May–Jun. 1985, 8(I), 399–401.

McIntosh HD, et al., "The Hemodynamic Consequences of Arrhythmias," *Prog Cardiovasc Dis.*, 8:330–363, 1966.

*Medtech Insight*, "Hot Topics in Heart Failure," Jun./Jul. 2004, 6(6/7).

Mehta et al., "Cardiology's 10 Greatest Discoveries of the 20$^{th}$ Century," *Texas Heart Journal*, 2002, vol. 9 No. 3.

Mercando et al., "Measurement of Differences in Timing and Sequence Between Two Ventricular Electrodes as a Means of Tachycardia Differentiation," *PACE*, Nov.–Dec. 1986, 9(II):1069–1078.
Mirowski M, et al., "A Chronically Implanted System for Automatic Defibrillation in Active Conscious Dogs," *Circulation*, Jul. 1975; 58(1):90–94.
Mirowski et al., "Clinical Experience with the Implantable Cardoverter–Defibrillator," *Annals of the New York Academy of Sciences*, 1984, 427:297–306.
Mirowski et al., "Clinical experience with the automatic implantable defibrillator," 39–42.
Mirowski et al., "The Automatic Implantable Cardioverter–Defibrillator," *PACE*, May–Jun. 1984, Part II, 7:534–540.
Mirowski et al., "Use of the automatic implantable cardioverter–defibrillator in the treatment of malignant ventricular tachyarrhythmias," *Herz*, 1984, 9(2):83–89.
Mirowski et al., "Clinical Performance of the Implantable Cardioverter–Defibrillator," *PACE*, Nov.–Dec. 1984, Part II, 7:1345–1350.
Molhoek et al., "QRS Duration and Shortening to Predict Clinical Response to Cardiac Resynchronization Therapy in Patients with End–Stage Heart Failure," *PACE*, Mar. 2004, 27:308–313.
Moore EN, et al., "Electrophysiological Studies on Pacing Techniques to Prevent Ventricular Fibrillation," *Nonpharmacological Therapy of Tachyarrhythmias*, 1987, 22:345–358.
Mortensen et al., "Sequential Biventricular Pacing: Evaluation of Safety and Efficacy," *PACE*, Mar. 2004, 27:339–345.
Moss, A, "Long–Term Pervenous Atrial Pacing From the Proximal Portion of the Coronary Vein," *JAMA*, Jul. 28, 1969, 543–545.
Moulopoulos et al., "Effect of Site and Intensity of Pacing on Left Ventricular Performance," Electocardiology 16(4), 1983, pp. 409–416.
Mower M, et al., "Unusual Patterns of Conduction Produced by Pacemaker Stimuli," *Am Heart J.*, Jul. 1967; 74(1):24–28.
Mower et al., "Automatic Implantable Cardioverter–Defibrillator Structural Characteristics," *Pacing Clin Electrophysiology.*, Nov. 1984; 7(6 Pt 2): 1331–1337.
Naito et al., "Atrial Alternans: Experimental Echocardiographic and Hemodynamic Demonstration During Programmed Pacing," *Am. J. of Cardiology*, Sep. 1981, pp. 468–472.
Navarro–Lopez et al., "Guideline 8. Criteria for Hospitalization," *Rev Esp. Cardiol.*, 1997;50 Suppl 1:47–48. (Spanish with English abstract).
Navarro–Lopez et al., "Guideline 1. Diagnosis Of Heart Failure And Ventricular Dysfunction," *Rev Esp Cardiol.*, 1997;50 Suppl 1:3–8 (Spanish with English abstract).
Navarro–Lopez et al., "Guideline 4. Treatment Of Heart Failure," *Rev Esp Cardiol.*, 1997;50 Suppl 1:27–31. (Spanish with English abstract).
Navarro–Lopez et al., "Guidelines For The Diagnosis And Management Of Heart Failure And Cardiogenic Shock," *Informe del Grupo de Trabajo de Insuficiencia Carddiacade la Sociedad Espannola de Cardiologia*] *Rev Esp Cardiol.*, 1999;52 Suppl 2:1–54. (Spanish with English abstract).
Ong et al., "Cephalic vein guide wire technique for implantation of permanent pacemakers," *American Heart Journal*, Oct. 1987, pp. 753–756.
Park et al., "Effect of Alteration of Left Ventricular Activation Sequence on the Left Ventricular End–Systolic Pressure–Volume Relation in Closed–Chest Dogs," *Circulation Research*, vol. 57, No. 5, Nov. 1985, pp. 706–717.
Patel et al., Letters To The Editor "Coronary Sinus Pacing," *Circulation*, vol. 58, No. 1, Jul. 1978, pp. 187–189.
Peschar et al., "Left Ventricular Septal and Apex Pacing for Optimal Pump Function in Canine Hearts," *Journal of the American College of Cardiology*, 2003, 41(7):1218–1226.
Platia et al., "Management of the Prolonged QT Syndrome and Recurrent Ventricular Fibrillation with an Implantable Automatic Cardioverter–Defibrillator," *Clinical Cardiology*, 1985, 8:490–493.
Platia et al. "Sensitivity of various extrastimuls techniques in patients with serious ventricular arrhythmias," *American Heart Journal*, Oct. 1983, 106(4):698–703.
Platia et al., "Treatment of Malignant Ventricular Arrhythmias With Endocardial Resection and Implantation of the Automatic Cardioverter–Defibrillator," *The New England Journal of Medicine*, Jan. 1986, 314(4):213–216.
Prinzen et al., "Relation Between the Pacing Induced Sequence of Activation and Left Ventricular Pump Function in Animals," *PACE*, Apr. 2002, Part I, 25(4):484–498.
Reid et al., "Automatic Implantable Cardioverter–Defibrillator Structural Characteristics," *PACE*, Nov.–Dec. 1984, Part II, 7:1338–1344.
Reid et al., "Clinical Evaluation of the Internal Automatic Cardioverter–Defibrillator in Survivors of Sudden Cardiac Death," *Am J Cardiol*. Jun. 1983;51(10):1608–1613.
Ritter, P., "Editorial," *PACE*, Jan. 2003, Part II, 26:136.
Rogel S, et al., "The Universal Pacer. A synchronized–demand pacemaker," *J Thorac Cardiovasc Surg.*, Mar. 1971; 61(3): 466–471.
Rosenheck et al., "Noninstrumental Pacemaker and Defibrillator Lead Removal: The Importance of the Rotation Forces," *PACE*, vol. 25, No. 7 Jul. 2002, pp. 1029–1036.
Rosenqvist et al., "Relative Importance of Activation Sequence Compared to Atrioventricular Synchrony in Left Ventricular Function," *Am. J. of Cardiology*, vol. 67, Jan. 15, 1991, pp. 148–156.
Santamore WP, et al., "A Theoretical and Experimental Model of Ventricular Interdependence," *Basic Res Cardiol.*, Sep.–Oct. 1986; 81(5):529–538.
Shefer et al., "Left Ventricular Function During Physiological Cardiac Pacing: Relation to Rate, Pacing Mode, and Underlying Myocardial Disease," *PACE*, vol. 10, Mar.–Apr. 1987, pp. 315–325.
Sodi–Pollares D, et al., "General Considerations About the Activation Process of the Heart," *Deductive and Polyparametric Electrocardiography*, 1970, 30–41.
Takeshita et al., "Effect of Intermittent Left Bundle Branch Block on Left Ventricular Performance," *Am. J. of Medicine*, vol. 58, Feb. 1974, pp. 251–255.
Tsagaris et al., "Species Variability in Hemodynamic Response to Paired–Pulse Stimulation," *Am. J. of Physiology*, Jun. 1969, pp. 1409–1417.
Tyers, GFO, et al., "A New Device for Nonoperative Repair of Internal Cardiac Pacemakers," *Archives of Surgery*, Jun. 1966, vol. 92:901–904.
Tyers, GFO, "Maximum Cardiac Performance After Complete Heart Block," *Surgical Forum*, vol. XVIII, American College of Surgeons, 1967, pp. 132–133.

Tyers, GFO, "Optimal electrode implantation site for asynchronous dipolar cardiac pacing," *Annals of Surgery*, Feb. 1968, 167(2), pp. 168–179, ISSN.
Tyers, GFO, et al., "An Integrated Program For Safe Permanent Internal Cardiac Pacing," *The Journal of Cardiovascular Surgery*, Barcelona, Sep. 27–29, 1973 pp. 163–166.
Tyers GFO, et al., "Effect of Site of Synchronous Unipolar Ventricular Stimulation and Volume Loading on Cardiac Function," *J Surg Res.*, Oct. 1973; 15(4):271–284.
Tyers, GFO, et al., "Comparative studies of 'state of the art' and presently used clinical cardiac pacemaker electrodes," *Journal of Thoracic and Cardiovascular Surgery*, St. Louis, vol. 67, No. 6, Jun. 1974 pp. 849–856.
Tyers, GFO, et al., Dept. Surg., Coll. Med., Milton S. Hershey Med. Cent., Pennsylvania State Univ., Hershey, Pa. 17033, "The Advantages of Transthoracic Placement of Permanent Cardiac Pacemaker Electrodes," *Journal of Thoracic and Cardiovascular Surgery*, 1975, 69/1 (pp. 8–16).
Tyers, GFO, et al., "The unfulfilled promise of demand pacing," *Journal of Thoracic and Cardiovascular Surgery*, Nov. 1976, 72(5) pp. 813–815.
Tyers, GFO, et al., "Improved R–wave Detection with Intramyocardial Electrodes," Department of Surgery, College of Medicine, the Milton S. Hershey Medical Center of the Pennsylvania State University, Hershey, PA 17033, 30$^{th}$ ACEMB, Los Angeles Hilton, Los Angeles, CA Nov. 5–9, 1977, p. 268.
Tyers, GFO, et al., Gorman I. Div. Cardiovascular Thoracic Surg. Dept. Surg., Univ. Texas Med. Branch, Galveston, TX 77550, "R–Wave Detection for Demand Pacing—The Superiority of Intramyocardial Over Endocardial Electrodes," *Journal of Surgical Research* (*J. Surg. Res.*), 1978, 24/4 (pp. 316–320).
Tyers, GFO, et al., "Myocardial Stimulation Impedance, The Effects Of Electrode Physiological And Stimulus Variables," *Annals of Thoracic Surgery*, 27 (1):pp. 63–69 1979.
Tyers, GFO, et al., "Multiprogrammable Pacemakers," *Canadian Journal of Surgery* (*Can. J. Surg*), 1981, 24/3 (pp. 252–256).
Tyers, GFO, et al., "Current Status And Future Of Programmable Pacing," Vogel, J.H.K. (Ed.). Cardiovascular Medicine, vol. 1. Raven Press: New York, N.Y., (1982).
Tyers, GFO, et al., "Current Status of Sensor–Modulated Rate–Adaptive Cardiac Pacing," *Journal of the American College of Cardiology*, 1990 15/2 (pp. 412–418).
Tyers, GFO, et al., "Medical Device Review In Canada," *PACE*, 1995, V18, No. 3 (Mar.).
Tyers, GFO, et al., "Coradial Bipolar Lead Implant and Follow–Up Experience," poster presentation at the North American Society for Pacing and Electrophysiology (NASPE), 17$^{th}$ Annual Scientific Sessions, Seattle, WA, May 15–18, 1996.
Tyers, GFO, et al., "Removal of Permanent Endocardial Pacing Leads (1981–1997)," *Heartweb*, vol. 4, No. 4, Feb. 1999 (Article No. 9920003), 1–8.
Tyers, GFO, et al., "Bipolar leads for use with permanently implantable cardiac pacing systems: A review of limitations of traditional and coaxial configurations and the development and testing of new conductor, insulation, and electrode designs," *Journal of Investigative Surgery* (*J. Invest. Surg.*) 1997, 10/1–2 (pp. 1–15).
Tyers, GFO, et al., "Similar indications but different methods: Should there be a consensus on optimal lead extraction techniques?", *PACE*, 2002, 25/7 (pp. 1019–1022).
Tyers, GFO, et al., "Bifocal/Biatrial Pacing in Clinical Practice," The XII World Congress on Cardiac Pacing & Electrophysiology, Hong Kong, Feb. 19–22, 2003 pp. 715–717.
Tyers, GFO, et al., "Coronary sinus lead extraction," *PACE*, Jan. 1, 2003, 26/1 II (pp. 524–526).
Tyers, GFO, et al., "Surgical Complications of Pacemaker Implant," *Clinical Cardiac Pacing and Electrophysiology, The XIIth World Congress on Cardiac Pacing and Electrophysiology*, Hong Kong Feb. 19–20, 2003, pp. 745–760.
Waldo, A, et al., "Ventricular Paired Pacing to Control Rapid Ventricular Heart Rate Following Open Heart Surgery," *Circulation*, vol. 53, No. 1, 1973, 176–181.
Watkins, Jr. et al., "Surgical Techniques for Implanting the Automatic Implantable Defibrillator," *PACE*, Nov.–Dec. 1984, Part II, 7:1338–1344.
Watkins et al., "The Treatment of Malignant Ventricular Arrhythmias with Combined Endocardial Resection and Implantation of the Automatic Defibrillator: Preliminary Report," *The Annals of Thoracic Surgery*, Jan.–Jun. 1984, 37:60–64.
Watkins et al., "Malignant Ventricular Arrhythmias," *The Annals of Thoracic Surgery*, Jan. 1984, 37(1):65–66.
Watkins et al., "Automatic Implantable Defibrillator," *The Journal of Thoracic and Cardiovascular Surgery*, Sep. 1983, 86(3):382–387.
Watkins et al., "Automatic Defibrillation in Man: Is It Feasible?"*The American Journal of Surgery*, Jun. 1983, 145:752–755.
Waxman, L, "Ventricular Pacing from the Middle Cardiac Vein Mimicking Supraventricular Morphology" *PACE*, vol. 2, Mar.–Apr. 1979.
Wish, M, et al., "Optimal Left Atrioventricular Sequence in Dual Chamber Pacing," *JACC*, vol. 3, Feb. 1984, p. 507 (Abstract).
Witte, J, et al., "Transvenous Atrial Synchronized Packing," *Advances in Pacemaker Technology*, 1975; 99–120.
Yoshimori, M, "An Experimental Study on the Site for Ventricular Pacing of A Dog Heart with Special Reference to Biventricular Pacing," *Nippon Ika Daigaku Zasshi*, vol. 54 No. 3 (1987) pp. 267–276. (Japanese with English–Language Abstract and English Translation Attached).
Zipes DP, et al., "Electrophysiologic Studies on Ventricular Fibrillation," *Cardiac Electrophysiology and Arrhythmias*, 1985, 317–320.

* cited by examiner

METHOD AND APPARATUS FOR TREATING HEMODYNAMIC DISFUNCTION

Matter enclosed in heavy brackets [ ] appears in the original patent but forms no part of this reissue specification; matter printed in italics indicates the additions made by reissue.

*CROSS REFERENCE TO RELATED APPLICATIONS*

*This is a continuation of Reissue application No. 08/547, 691, filed Oct. 19, 1995 now U.S. Pat. No. RE 38,119 E, which is a continuation of Reissue application No. 07/890, 280, filed May 29, 1992* now abandoned, which is a reissue of U.S. Pat. No. 4,928,688, all of which are incorporated herein by reference.

BACKGROUND OF THE INVENTION

I. Field of the Invention

This invention pertains to medical devices, but more specifically, to a method for increasing the cardiac output of a patient suffering from congestive heart failure by stimulating the heart of the patient at multiple sites simultaneously.

II. Discussion of the Prior Art

Normally, impulses from the SA node affect contraction of the atria and then propagate to the AV node. The AV node, in turn, emits a second nerve impulse which affects contraction of the ventricles. These nerve impulses affect contraction, i.e., depolarization of the tissue of the heart, in a coordinated manner to circulate blood through the body. Cardiac pacers of the type herein described generally are useful for maintaining proper functional operation of a sick heart. Of many cardiac deficiencies which have in the past been diagnosed and treated, conduction difficulties have presented significant problems for which a pacer has been used for treatment. A particular conduction deficiency, known as AV branch block, inhibits the transfer of nerve impulses from the sinoatrial (SA) node to atrial-ventricular (AV) node. When a bundle block occurs, these nerve impulses are not properly transmitted from the SA node to the AV node and ventricles.

When this condition occurs, normal treatment is to employ a pacer which locks onto the rhythmic cycle of a atrial beating signal and supplies to the ventricles a stimulating impulse at a certain time thereafter to effect contraction of the ventricles. The time period between the occurrence of the atrial beat and the normal contraction of the ventricles is known as the A-V delay period. Generally, hemodynamic efficiency is somewhat dependent to the A-V delay period, thus the pacer must emit a stimulating pulse at a time to preserve an optimum A-V delay period.

Other forms of conduction deficiency, such as myocardial scarring and bundle branch block, cause slow conduction of nerve impulses, in which case, nerve impulses are indeed passed from the SA to the AV node, but in a time period which is slower than normal. The Q-R-S complex in this case would manifest itself in being very wide and hemodynamic efficiency also becomes lower than normal.

In each of the above-mentioned cardiac deficiencies, the heart does not contract in coordinated fashion. This uncoordinated movement increases depolarization time and results in more inefficient pumping rather than a more coordinated and simultaneous ventricular depolarization. In essence, such conduction deficiencies result in asynchrony between the left and right ventricle.

Additionally, arrhythmias of the heart produce uncoordinated ventricular contraction that affects the hemodynamic efficiency of the heart. Specifically, the recent paper "Incomplete Filling and Incoordinate Contraction as Mechanisms of Hypotension During Ventricular Tachycardia in Man", published in Circulation, Vol. 68, No. 5, in 1983, describes that left ventricular function is severely disturbed by the disorganization of wall motion in hearts undergoing ventricular tachycardias. Moreover, it was found that hearts with impaired functions show profound reductions in pumping ability due to incoordinate contraction of the ventricles. It appears reasonable to believe, therefore, that any abnormal functioning heart that requires pacemaking or which has QRS widening will have a better hemodynamic efficiency if both ventricles are paced to contract in coordination with each other. There have been systems developed in the past employing a plurality of electrodes attached to the heart for effecting stimulation of a plurality of regions of the heart. For example, the Funke U.S. Pat. No. 3,937,226 discloses a cardiac electrical stimulation defibrillation system including a plurality of electrode terminals connected in a spaced relation on the heart. The electrodes, which provide stimulating and sensing, are each connected to amplifiers. The amplifiers are connected to electronic control circuit means configured to cause stimulation of all of the electrode terminals simultaneously in response to a sensed depolrization signal on the heart by at least one electrode terminal. In addition, the electronic control circuit is provided with a multivibrator means to synchronize the stimulation signal with the Q-R-S complex. Although Funke does teach the concept of simultaneous stimulation of a plurality of spaced electrodes, he does not disclose its specific use as a method of improving the cardiac output of patients suffering from congestive heart failure, nor does he discuss the specfic placement of the electrodes about the heart.

The Rockland et al U.S. Pat. No. 4,088,140 discloses a similar system to Funke's although a specific use as a pacemaker is stated in the patent. Rockland, et al discloses a demand anti-arrythmia pacemaker including a plurality of sensing electrodes connected to the heart to sense ventricular depolarizations. Electronic circuitry is provided having two paths of operation. A first path provides stimulation to one area of the heart if depolarization of a naturally occurring heart beat fails to occur within a first predetermined time period. In this first path, it is stated that the circuitry acts as a pacemaker in the event of skipped natural heartbeats. A second path provides stimulation to a plurality of locations on the heart if a depolarization signal is sensed on the heart within a second predetermined time period. In this second path, it is stated that the circuitry acts as a synchronous multiple electrode pacemaker or a synchronous multiple electrode defibrillator. Although, one example of an electrode placed in the intraventricular section and others in a spaced relation on the heart ventricles is given, there are no teachings of the specific placement of the electrodes on the heart nor the improvement of cardiac output from a sick heart. In addition, the electrodes perform either stimulating or sensing, not both, therefore a large number of electrodes is required in this system.

The Tacker, Jr. et al and McCorkle U.S. Pat. Nos. 4,548, 203, 4,458,677 and 4,332,259, respectively, disclose the specific placement of an electrode in or around both left and right ventricles of the heart. The Tacker, Jr. et al patent discloses the placement of a catheter having one electrode in the right ventricle and another outside the heart and a third electrode placed on the left ventricle. The catheter electrodes, each being paired with the left ventricular electrode, are pulsed in sequence with a predetermined time separation resulting in uniform current density delivered to the heart. However, this pulsing scheme and configuration is disclosed for use in a ventricular defibrillation device and not for cardiac pacing to improve cardiac output wherein a more precise synchronization of stimulation signals with the Q-R-S complex is required.

The McCorkle, Jr. patents disclose the specific placement of an electrode in the right ventricle and another electrode in the coronary sinus surrounding the left ventricle for connection to a pacemaker. However, there is no specific technique disclose of providing stimulating signals to the electrodes to perform a pacemaking function.

In light of the above difficulties and shortcomings of the prior art, an objective of the present invention is to provide a cardiac pacer for increasing hemodynamic efficiency of a heart experiencing a conduction deficiency.

Another objective of the invention is to ensure a more coordinated and simultaneous ventricular depolarization of both left and right ventricles of the heart.

A yet further objective of this invention is to provide a cardiac pacer suitable for being implanted in a manner so as to impose a minimal surgical risk during implantation thereof.

A further objective of this invention is to provide a method and apparatus of separately sensing and stimulating each ventricle of the heart in order for effecting simultaneous contraction automatically of both ventricles of the heart to narrow the QRS complex of a failing heart and thereby cause an increase in blood pressure and cardiac output.

SUMMARY OF THE INVENTION

The method of the present invention involves a procedure for pacing of the heart in a particular way so as to improve its contraction pattern, and thereby augment the movement of blood through the heart. Patients suffering from severe congestive heart failure, which is found not to respond well to conventional drug therapy and to have a conduction defect in the ventricle resulting in a widen Q-R-S complex have been aided by a pacing regimen in which stimulating pulses are simultaneously applied to both ventricles by way of a demand pacemaker or asynchronous pacemaker.

It is theorized that a considerable part of the hemodynamic impairment in refractory congestive heart failure with conduction defects is due to an incoordinate contraction of the heart, so that a part of the heart muscle contracts and balloons out the part that is not contracting. When the latter area of the heart muscle does finally contract, the former has relaxed, so that a large part of the blood volume is merely shunted back and forth within the heart rather than being ejected as would happen with a more coordinate contraction pattern.

To attain the foregoing and other objectives, the present invention comprises, a bi-ventricular cardiac pacer having detecting and stimulating circuits for effecting substatially simultaneous contraction of both left and right ventricles of the heart. In the preferred embodiment, the bi-ventricular pacer comprises ECG amplifier means for separately processing sensed cardiac signals from each of the right and left ventricles. The amplified sensed signals are used to determined where possible abnormal conduction delays exist on the heart and to activate an electrical stimulator for stimulating the appropriate abnormally functioning part of the heart. More specifically, the stimulator responds to the control circuit to issue stimulating pulses simultaneously to either the left or right ventricle, as appropriate. The stimulator may be of the demand type wherein pacing pulses are only issued in the absence of a normal Q-R-S complex for one or the other of the two ventricles (e.g., occasional bundle branch block or slow conduction), or the nondemand type wherein pacing pulses are always issued (e.g., permanent bundle branch block or slow conduction).

To convey and sense signals to and from the heart, the present invention includes a pacing lead assembly comprising first and second separate electrodes. The first electrode is preferably introduced through the superior vena cava into the right ventricle and the second electrode is introduced through the coronary sinus to the left ventricle. Both lead segments include a sensing and pacing tip electrode which serves to both sense a cardiac depolarization signal or to apply a stimulating pulse from an implanted pulse generator to the ventricle.

Additionally, to preserve a predetermined A-V delay period, additional atrial sensing electrodes may be placed on or around the atrial chambers of the heart and connected to the control circuit. The control circuit responds to the sensed atrial and ventricular depolarization signals to provide simultaneous ventricular contraction signals applied to the left and right ventricles following a preset A-V delay period.

The advantages of the present invention include a more precise and coordinated simultaneous ventricular depolarization of both the right and left ventricular to thereby increase hemodynamic efficiency of a patient experiencing congestive heart failure or weak contractions.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWING FIGURES

Figure 2:
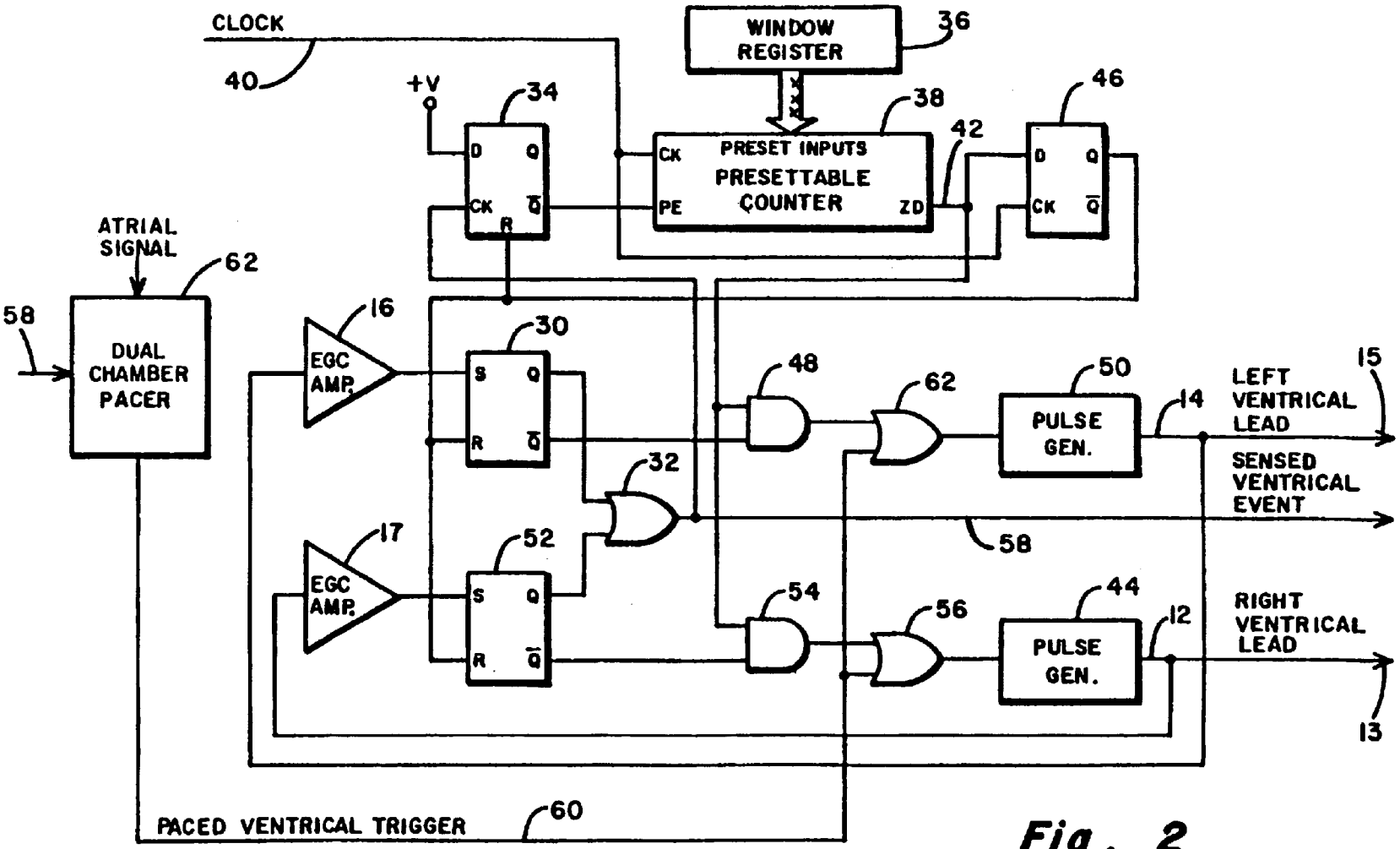

FIG. 1 depicts a functional block diagram of an apparatus for carrying out the teachings of this invention; and FIG. 2 is a logic diagram of the "CONTROL" shown in FIG. 1.

DETAILED DESCRIPTION OF THE PREFERRED EMBODIMENT

FIG. 1 illustrates the overall pacing system which may be employed for carrying out the teachings of the invention. A pair of leads 12 and 14 with corresponding sensing/stimulating tip electrodes 13 and 15 are electrically connected, via conductors 18 and 21, to separate ECG sense amplifiers 16 and 17 (or to a single multiplexed amplifier). The amplifiers 16 and 17 are both connected to a control circuit unit 20. A stimulator circuit 22 is connected to the control unit 20 and has two output conductor lines 24 and 26 which are electrically connected to the conductors 18 and 21, respectively. From this structure, signals may be separately sensed by the electrodes 13 and 15 and stimulating pacing signals may be separately delivered to the electrodes 13 and 15, via lead branches 12 and 14.

In operation, the electrodes 13 and 15 are disposed in or about the right and left ventricles, respectively. A preferred surgical procedure for-implanting the lead 12 is to extend it through the superior vena cava 28 so that the sensing stimulating tip 13 thereof lodges in the internal chamber of the right ventricle of the heart 10. A preferred surgical-procedure for implanting lead branch 14 is to extend it through the coronary sinus (not shown) of the heart 10 so that the sensing/stimulating tip 15 thereof lodges directly in or about the coronary sinus and left ventricle. Although it is described that electrodes 13 and 15 perform both sensing and pacing, it is possible for testing and examination, that separate unipolar or bipolar sensing and stimulating electrodes may be used.

When attached to the heart, the electrodes 13 and 15 sense cardiac signals in the form of well-known Q-R-S complex at separate sites within the left and right ventricles. The ECG amplifiers 16 and 17 feed the amplified versions of these signals to the control circuit 20.

The control circuit 20 analyzes the cardiac signals to determine whether an abnormal conduction exists. Specifically, if a cardiac signal is received from the left ventricle but not from the right ventricle, the control circuit 20 provides a control signal to the stimulator 22 to issue a stimulating pacing pulse over conductors 24 and 18 and lead branch 12 to the right ventricle, via the sensing/stimulating tip electrodes 13. Similarly, the control circuit 20 provides a control signal to the stimulator 22 to issue a stimulating pacing pulse over lead branch 14 to the left ventricle, via sensing/stimulating tip electrode 15, if a cardiac depolarization signal is received from the right ventricle, but not from the left ventricle. It is also possible to sense a depolarization signal from only one ventricular chamber and then unconditionally stimulate both ventricular chambers. This is wasteful of power which is a concern only if the stimulator is totally implanted and must rely on an implanted battery power source.

The timing of the stimulating pacing pulse from the stimulator 22 is such that both ventricles will contract substantially simultaneously. Where both ventricles are unconditionally stimulated upon the occurrence of a QRS complex on only one side, the fact that ventricular site which had produced a Q-R-S complex is immediately stimulated along with the other ventricle does not cause a problem since the site producing that complex is still refractory at the time it is stimulated.

It is also possible that no cardiac signals are sensed from either ventricle, possibly resulting from complete conduction failure between the sinoatrial node and the atrialventricular node. In this case, the control circuit 20 will again activate the stimulator 22 to provide stimulating signals to both ventricles simultaneously.

In an alternative embodiment of the invention, the issuance of pacing pulses to the ventricles is time-coupled to the rhythmic cycle of the atrial beat of the heart to preserve a preset atrial-ventricular delay period of about 120 to 200 milliseconds. Additional atrial sensing is accomplished, via lead 23 and a sense electrode 25 similar to the ventricular leads 12 and 14, but disposed in or about the right atrial chamber and connected to the control circuit 20, via atrial sense amplifier 27. The control circuit 20 may be configured to respond to the sensed atrial and ventricular signals to activate the stimulator for providing appropriate simultaneous stimulating signals to the ventricles as described above in accordance with the predetermined A-V delay period.

In the case where the conduction of the natural stimulating signal originating at the sinoatrial node of the heart 10 is only partially blocked or slowed, the ventricles may partially or incompletely contract, in which case hemodynamic efficiency is reduced. Under these circumstances, provision is made in the control circuit 20 for determining whether a Q-R-S cardiac signal, although present, is weak or slow, and if so, to activate the stimulator 22 to stimulate the ventricles of the heart by passing pacing pulses simultaneously thereto.

FIG. 2 shows one embodiment of the control circuitry 20 of FIG. 1 required to perform bi-ventricular pacing. Also shown in the circuit of FIG. 2 are means for interconnecting the bi-ventricular control circuitry with conventional demand pacing circuitry to implement various additional pacing modes. It is understood that in the preferred embodiment, the circuitry shown in FIG. 1 would be preferably incorporated directly into the design of a pacer rather than its adjunctive form shown here for purposes of illustration.

To accomplish bi-ventricular pacing, activity is sensed in both the left and the right ventricle. When a ventricular contraction is sensed in either ventricle, a timer is initiated. If within a time window established by said timer, the contraction is sensed in the other ventricle, all pacing is inhibited because the natural contractions are deemed to be simultaneous. On the other hand, if ventricular contractions are not sensed in both ventricles within a period of coincidence defined by the time delay, at the end of this delay, the pacing pulse will be emitted, but only to the ventricle for which a QRS complex has not been sensed. Generally, ventricular contractions which occur within 5–10 milliseconds of each other result in sufficient hemodynamic efficiency so as to not require treatment. Hence, the delay window may be of this order of magnitude. As used herein, the term "substantially simultaneous contraction" includes the occurrence of natural contractions of both ventricles within the window period or an evoked contraction of one or both ventricles immediately following the expiration of the window period.

Operation of the circuit of FIG. 2 will now be described. Electrical activity originating in the left ventricle is sensed by electrode 15 on lead 14 coupled to amplifier 16. It is assumed that amplifier 16 contains all of the thresholding and inhibiting provisions commonly utilized in existing pacing systems to inhibit all electrical activity, save valid ventricular contractions. Similarly, electrical activity in the right ventricle is sensed by electrode 13 on lead 12 and processed by ECG amplifier 17.

Let if first be assumed that a left ventricle contraction procedes that of the right. In this case, an R-wave signal propagates through amplifier 16 to set the Set-Reset type flip-flop 30. a logical "1" signal passes through OR gate 32 to clock D-type of flop 34 to the "set" state which, in turn, initiates the aforementioned delay timing. Window register 36 is loaded with a digital count value which is representative of the desired delay window, e.g., 5–10 ms. This may be either a fixed, hard-wired register or, alternatively, a programmable register which may be set by telemetry means in a known manner. When the preset enable input (PE) in high, counter 38 is held at a digital count corresponding to the value held in window register 36. When flip-flop 34 is set, the PE on counter 38 is removed, allowing the counter to be decremented with each clock pulse provided on clock line 40. At the end of the preprogrammed window delay interval, counter 38 is decremented to zero, causing the zero detect (ZD) line 42 to go high. The leading edge of the zero detect pulse is used to trigger a ventricle pacing pulse from pulse generator 44, via gates 54 and 56, as required. The pulse generator circuitry 44 converts this leading edge trigger to a pulse of the proper amplitube and duration for effective stimulation of the right ventricle. Note that, since under the assumed conditions flip-flop 30 has been set, AND gate 48 is disabled and, therefore, pulse generator 50 is inhibited from generating a left ventricle pacing pulse.

Next to be considered is the case where a right ventricle contraction has not been sensed within the prescribed window interval. In this case, flip-flop 52 remains reset and AND gate 54 is enabled which allows the zero detect pulse ZD to propagate through OR gate 56 to trigger pulse generator 44, thus stimulating the right ventricle. If, however, a right ventricle contraction has been detected, flip-flop 52 would have been set prior to the generation of the ZD pulse and, in this case, both AND gates 48 and 54 are disabled and no pacing pulse in either ventricle is generated.

It can be seen from the symmetry of the circuit that the operation is identical if the right ventricle contraction precedes the left ventricle contraction by more than the preprogrammed delay interval. In either case, the setting of either flip-flop 30 or 52 causes 52 causes the initiation of the timing window delay interval. When one of these flip-flop sets, the other must set within the window period, otherwise a pacing pulse will be generated in the unsensed ventricle.

The bi-ventriclar pacing control circuitry may be combined with other well-known pacer control circuitry such that the bi-ventriclar mode can be realized in combination with any other pacing mode, such as VVI, DDD, VOO. Line 58 is the logical OR of either of left ventricle event or a right ventricle event. It may be connected to other pacing control circuitry 62 in place of the signal which is normally responsive to only activity in the left ventricle. A sensed ventricle event thus inhibits the generation of a pacing trigger from another pacing circuitry and leaves the control of pacing in the alternate ventricle, as required, to the circuitry of FIG. 1. If line 58 is not activated within the escape interval of the other pacing control circuitry, a paced ventricle trigger signal on line 60 is produced which propagates through both OR gate 62 and OR gate 56 to trigger pacing pulses in both ventricles.

It is also contemplated that when a ventricular depolarization signal is sensed in one or the other of the ventricles, that a stimulating pulse may also be immediately delivered, on an unconditional basis, to both ventricles, via the implanted leads 13 and 15, thus resulting in a coordinated contraction of both ventricles.

The foregoing illustrate preferred arrangements for carrying out the objectives of this invention. Modifications and variations can obviously be made by those skilled in the art without departing from the true spirit and scope of the invention. For instance, the circuit may be employed to simultaneously pace the auricles, instead of ventricles, if such is required to improve pumping efficiency. The arrangement may also be employed as an improvement of conventional pacers thereby to improve their performance. As stated herein, the inventive arrangement can be used in an implanted device or in an external treating, diagnostic or testing device. Accordingly, the invention is limited only by the scope of the appended claims rather than by what is shown and described. Therefore, it is the intent to cover all such modifications and alternate embodiments as may come within the true scope of this invention.

What is claimed is:

[1. A method for improving the hemodynamic efficiency of a sick heart comprising the steps of:

(a) detecting respective cardiac signals originating in the left and right ventricles of the heart;

(b) analyzing said cardiac signals and the absence thereof in an electronic control circuit; and (c) providing electrical pulses from a stimulating circuit controlled by said control circuit to one, the other or both ventricles as required for effecting substantially simultaneous contraction of both ventricles, said step of analyzing including providing a control signal from said control circuit to said stimulating circuit for producing an electrical stimulating pulse to one or both ventricles in response to the absence of a detected cardiac signal from one or both ventricles within a time interval which is a small fraction of the pulse width of a detected cardiac signal.]

[2. The method of claim 1 wherein said step of detecting respective cardiac signals comprises deposing electrodes in or on the left and right ventricles for separately detecting the respective cardiac signals of the left and right ventricles, and applying said cardiac signals to separate ECG amplifier means connected to each of said electrodes to amplify the cardiac signal for analysis.]

[3. The method of claim 2 wherein said step of providing electrical pulses includes delivering an electrical pulse from said stimulating circuit to said electrodes in or on both the left and right ventricles.]

[4. The method of claim 1 wherein said step of analyzing further includes providing a control signal from said control circuit to the stimulating circuit to produce an electrical stimulating pulse to the left ventricle in the absence of a detected cardiac signal from the left ventricle, or to the right ventricle in the absence of a detected cardiac signal from the right ventricle, or to both ventricles in the absence of detected cardiac signals from both ventricles.]

[5. A method for effecting simultaneous contraction of both left and right ventricles of a heart for improving hemodynamic efficiency comprising the steps of:

separately sensing for the presence of cardiac depolarization signals from both left and right ventricles;

determining whether said cardiac depolarization signals are simultaneously present in both the left and right ventricles; and stimulating at least one ventricle substantially simultaneously with the contraction of at least one other ventricle in the event that said cardiac depolarization signals are determined not to be simultaneously present in both ventricles.]

[6. A method of effecting simultaneous contraction of both left and right ventricles of a heart for improving hemodynamic efficiency comprising the steps of:

sensing the cardiac signals of the atria and separately sensing the cardiac depolarization signals of both the left and right ventricles;

determining whether said cardiac depolarization signals are simultaneously present in both the left and right ventricles;

stimulating at least one ventricle simultaneously with the contraction of at least one other ventricle after a predetermined A-V period in the event that said cardiac depolarization signals are determined not to be simultaneously present in both ventricles.]

[7. A method of increasing the cardiac output of a sick heart comprising the steps of:

(a) implanting a pacing lead having at least two sensing/pacing electrodes in the body such that one of said sensing/pacing electrodes is in or on the right ventricle and the other of said sensing/ pacing electrodes is in or on the left ventricle;

(b) sensing depolarization signals picked up by said sensing/pacing electrodes upon their occurrence;

(c) determining whether the depolarization signals sensed in step (b) fail to occur within a predetermined time interval of one another and, if so;

(d) applying an electrical stimulating pulse to the sensing/pacing electrode associated with the ventricle not producing a depolarization signal within said time interval at the conclusion of said time interval.]

[8. The method as in claim 7 wherein said predetermined time interval is in the range of from about 5 ms. to 10 ms.]

[9. A bi-ventricular pacemaker, comprising:

(a) sense means for sensing ventricular depolarization signals originating in or on the right and left ventricles;

(b) means coupled to said sense means for initiating a time delay of a predetermined length which is short compared to the period of a QRS complex upon detection of a ventricular depolarization signal in one of said right or left ventricles; and (c) pulse generator means operative upon the termination of said time delay for producing a ventricular simulating pulse and applying same to the other of said right or left ventricles unless a ventricular depolarization signal occurs in said other of said right of left ventricle prior to the expiration of said time delay.]

[10. The bi-ventricular pacemaker as in claim 9 wherein said sense means comprises a bi-ventricular lead having a first electrode for contacting the right ventricle and a second electrode for contacting the left ventricle and sense amplifier means electrically coupled to said first and second electrodes.]

[11. The bi-ventricular pacemaker as in claim 10 wherein said means coupled to said sense means includes:

(a) first and second set-reset flip-flop connected to be set by an output from said sense amplifier means;

(b) presetable counter means for initially containing a digital value representative of said time delay;

(c) means for incrementing or decrementing said digital value in said presettable counter means at regular intervals until a predetermined count is reached;

(d) means responsive to the value in said counter means reaching said predetermined count for producing a control signal;

(e) logic means coupled to said first and second flip-flops and to said presettable counter means for receiving said control signals; and wherein (f) said pulse generator means is enabled by said logic means.]

[12. The bi-ventricular pacemaker as in claim 11 wherein said pulse generator means is coupled to said first and second electrodes.]

[13. An atrial-coupled, bi-ventricular pacemaker for implantation or external use comprising atrial and ventricular sensing means for detecting cardiac signals, said sensing means including first and second ventricular electrodes connected in series for sensing and stimulating the right and the left ventricles, respectively, and an atrial electrode adapted to be disposed in an atrial chamber for detecting cardiac signals of the atria, all of said electrodes being connected to separate ECG amplifier means for amplifying the sensed signals; a control circuit coupled to said ECG amplifier means for analyzing the cardiac signals picked up by said sensing means and providing a control signal; and a stimulating circuit means for producing an electrical stimulating pulse to the left ventricle in the absence of a detected cardiac signal from the left ventricle, and to the right ventricle in the absence of a detected cardiac signal from the right ventricle, and to both ventricles in the absence of detected cardiac signals from both ventricles to effect substantially simultaneous contraction of both ventricles after a predetermined A-V delay period.]

[14. The pacemaker of claim 13 wherein said first electrode is adapted to be placed in the right ventricle and the second electrode is adapted to be placed in the coronary sinus extending about the left ventricle.

*15. A heart stimulating device for treating heart failure, comprising:*

*a sense amplifier to receive ventricular depolarization signals originating from a first ventricle;*

*a pulse generator, connected to the sense amplifier, to generate a stimulating pulse in the event the sense amplifier receives a ventricular depolarization signal; and*

*an electrode, connected to the pulse generator, to apply the stimulating pulse to a second ventricle in the event the sense amplifier receives a ventricular depolarization signal.*

*16. The heart stimulating device of claim 15, the electrode further comprising:*

*an electrode adapted to be disposed in or about the right ventricle to sense ventricular depolarization signals originating from the right ventricle.*

*17. The heart stimulating device of claim 15, wherein the sense amplifier receives ventricular depolarization signals originating from the right ventricle.*

*18. The heart stimulating device of claim 17, wherein the electrode connected to the pulse generator applies the stimulating pulse to the left ventricle.*

*19. The heart stimulating device of claim 15, the electrode further comprising:*

*an electrode adapted to be disposed in or about the left ventricle to sense ventricular depolarization signals originating from the left ventricle.*

*20. The heart stimulating device of claim 15, wherein the sense amplifier receives ventricular depolarization signals originating from the left ventricle.*

*21. The heart stimulating device of claim 20, wherein the electrode connected to the pulse generator applies the stimulating pulse to the right ventricle.*

*22. The heart stimulating device of claim 15, wherein the pulse generator generates the stimulating pulses immediately after the sense amplifier receives a ventricular depolarization signal.*

*23. The heart stimulating device of claim 15, further comprising:*

*a timer to initiate a delay period after the sense amplifier receives a ventricular depolarization signal.*

*24. The heart stimulating device of claim 23, wherein the pulse generator generates the stimulating pulse after the delay period.*

*25. The heart stimulating device of claim 15, wherein the sense amplifier receives ventricular depolarization signals from both the right ventricle and the left ventricle.*

*26. The heart stimulating device of claim 15, wherein the pulse generator generates stimulating pulses for both the right ventricle and the left ventricle.*

*27. A heart stimulating device for treating heart failure, comprising:*

*means for receiving ventricular depolarization signals originating from a first ventricle;*

*means for generating a stimulating pulse in the event the receiving means receives a ventricular depolarization signal; and*

*means for applying the stimulating pulse to a second ventricle in the event the receiving means receives a ventricular depolarization signal.*

*28. The heart stimulating device of claim 27, the receiving means further comprising:*

*an electrode means adapted to be disposed in or about the right ventricle for sensing ventricular depolarization signals originating from the right ventricle.*

*29. The heart stimulating device of claim 28, wherein the applying means applies the stimulating pulse to the left ventricle.*

*30. The heart stimulating device of claim 28, wherein the applying means applies stimulating pulses to both the left ventricle and the right ventricle.*

*31. The heart stimulating device of claim 27, the receiving means further comprising:*

*an electrode means adapted to be disposed in or about the left ventricle for sensing ventricular depolarization signals originating from the left ventricle.*

*32. The heart stimulating device of claim 31, wherein the applying means applies the stimulating pulse to the right ventricle.*

*33. The heart stimulating device of claim 31, wherein the applying means applies stimulating pulses to both the left ventricle and the right ventricle.*

*34. The heart stimulating device of claim 27, wherein the generator means generates the stimulating pulses immediately after the receiving means receives a ventricular depolarization signal.*

*35. The heart stimulating device of claim 27, further comprising:*

*means for initiating a delay period after the receiving means receives a ventricular depolarization signal.*

*36. The heart stimulating device of claim 35, wherein the generator means generates the stimulating pulse after the delay period.*

*37. The heart stimulating device of claim 27, wherein the receiving means receives ventricular depolarization signals from both the right ventricle and the left ventricle.*

*38. The heart stimulating device of claim 27, wherein the generator means generates stimulating pulses for both the right ventricle and the left ventricle.*

*39. A method for improving the hemodynamic efficiency of a heart, comprising:*

*receiving ventricular depolarization signals originating from a first ventricle;*

*generating a stimulating pulse in response to the receiving of a ventricular depolarization signal; and*

*applying the stimulating pulse to a second ventricle in response to the receiving of a ventricular depolarization signal.*

*40. The method of claim 39, the receiving further comprising:*

*receiving ventricular depolarization signals originating from the right ventricle.*

*41. The method of claim 40, the applying further comprising:*

*applying the stimulating pulse to the left ventricle.*

*42. The method of claim 40, the applying further comprising:*

*applying stimulating pulses to both the left ventricle and the right ventricle.*

*43. The method of claim 39, the receiving further comprising:*

*sensing ventricular depolarization signals originating from the left ventricle.*

*44. The method of claim 43, the applying further comprising:*

*applying the stimulating pulse to the right ventricle.*

*45. The method of claim 43, the applying further comprising:*

*applying stimulating pulses to both the left ventricle and the right ventricle.*

*46. The method of claim 39, the generating further comprising:*

*generating the stimulating pulses immediately after receiving a ventricular depolarization signal.*

*47. The method of claim 39, further comprising:*

*initiating a delay period after receiving a ventricular depolarization signal.*

*48. The method of claim 47, the generating further comprising:*

*generating the stimulating pulse after the delay period.*

*49. The method of claim 39, the receiving further comprising:*

*receiving ventricular depolarization signals from both the right ventricle and the left ventricle.*

*50. The heart stimulating device of claim 39, the generating further comprising:*

*generating stimulating pulses for both the right ventricle and the left ventricle.*

*51. A heart stimulating device for treating heart failure comprising:*

*an electrode to sense a cardiac depolarization signal from a first ventricle;*

*a sense amplifier, connected to the electrode, to process the cardiac depolarization signal; and*

*a stimulator, connected to the sense amplifier, to issue a stimulating pulse to a second ventricle in response to the ventricular cardiac depolarization signal.*

*52. The heart stimulating device of claim 51, wherein the electrode senses a cardiac depolarization signal from the right ventricle.*

*53. The heart stimulating device of claim 52, wherein the stimulator issues a stimulating pulse to the left ventricle in response to sensing a cardiac depolarization signal from the right ventricle.*

*54. The heart stimulating device of claim 52, wherein the stimulator issues stimulating pulses to both ventricles in response to sensing a cardiac depolarization signal from the right ventricle.*

*55. The heart stimulating device of claim 51, wherein the electrode senses a cardiac depolarization signal from the left ventricle.*

*56. The heart stimulating device of claim 55, wherein the stimulator issues a stimulating pulse to the right ventricle in response to sensing a cardiac depolarization signal from the left ventricle.*

*57. The heart stimulating device of claim 55, wherein the stimulator issues stimulating pulses to both ventricles in response to sensing a cardiac depolarization signal from the left ventricle.*

*58. The heart stimulating device of claim 51, wherein the stimulator issues the stimulating pulse immediately after the electrode senses a ventricle depolarization signal.*

*59. The heart stimulating device of claim 51, further comprising:*

*a timer to initiate a delay period after the electrode senses a ventricular depolarization signal.*

*60. The heart stimulating device of claim 59, wherein the stimulator issues the stimulating pulse after the delay period.*

*61. The heart stimulating device of claim 51, wherein the sense amplifier processes cardiac depolarization signals received from both the right ventricle and the left ventricle.*

*62. A heart stimulating device for treating heart failure comprising:*

*means for sensing a cardiac depolarization signal from a first ventricle;*

*means, connected to the sensing means, for receiving the cardiac depolarization signal; and*

*means, connected to the receiving means, for issuing a stimulating pulse to a second ventricle in response to the ventricular cardiac depolarization signal.*

*63. The heart stimulating device of claim 62, wherein the sensing means senses a cardiac depolarization signal from the right ventricle.*

*64. The heart stimulating device of claim 63, wherein the issuing means issues a stimulating pulse to the left ventricle in response to sensing a cardiac depolarization signal from the right ventricle.*

*65. The heart stimulating device of claim 63, wherein the issuing means issues stimulating pulses to both ventricles in response to sensing a cardiac depolarization signal from the right ventricle.*

*66. The heart stimulating device of claim 62, wherein the sensing means senses a cardiac depolarization signal from the left ventricle.*

*67. The heart stimulating device of claim 66, wherein the issuing means issues a stimulating pulse to the right ventricle in response to sensing a cardiac depolarization signal from the left ventricle.*

*68. The heart stimulating device of claim 66, wherein the issuing means issues stimulating pulses to both ventricles in response to sensing a cardiac depolarization signal from the left ventricle.*

*69. The heart stimulating device of claim 62, wherein the issuing means issues the stimulating pulse immediately after the electrode senses a ventricular depolarization signal.*

*70. The heart stimulating device of claim 62, further comprising:*

*means for initiating a delay period after the electrode senses a ventricular depolarization signal.*

*71. The heart stimulating device of claim 70, wherein the issuing means issues the stimulating pulse after the delay period.*

*72. The heart stimulating device of claim 62, wherein the receiving means receives cardiac depolarization signals from both the right ventricle and the left ventricle.*

*73. A method for improving the hemodynamic efficiency of a heart, comprising:*

*sensing a cardiac depolarization signal from a first ventricle;*

*receiving the ventricular cardiac depolarization signal; and*

*issuing a stimulating pulse to a second ventricle in response to the ventricular cardiac depolarization signal.*

*74. The method of claim 73, the sensing further comprising:*

*sensing a cardiac depolarization signal from the right ventricle.*

*75. The method of claim 74, the issuing further comprising:*

*issuing a stimulating pulse to the left ventricle in response to sensing a cardiac depolarization signal from the right ventricle.*

*76. The method of claim 74, the issuing further comprising:*

*issuing stimulating pulses to both ventricles in response to sensing a cardiac depolarization signal from the right ventricle.*

*77. The method of claim 73, the sensing further comprising:*

*sensing a cardiac depolarization signal from the left ventricle.*

*78. The method of claim 77, the issuing further comprising:*

*issuing a stimulating pulse to the right ventricle in response to sensing a cardiac depolarization signal from the left ventricle.*

*79. The method of claim 77, the issuing further comprising:*

*issuing stimulating pulses to both ventricles in response to sensing a cardiac depolarization signal from the left ventricle.*

*80. The method of claim 73, the issuing further comprising:*

*issuing the stimulating pulse immediately after the sensing of the ventricular depolarization signal.*

*81. The method of claim 73, further comprising:*

*initiating a delay period after the sensing of the ventricular depolarization signal.*

*82. The method of claim 81, the issuing further comprising:*

*issuing the stimulating pulse after the delay period.*

*83. The method of claim 73, the receiving further comprising:*

*receiving ventricular cardiac depolarization signals from both the left and the right ventricles.*

*84. A heart stimulating device for treating heart failure, comprising:*

*an electrode to sense ventricular depolarization signals originating from the right ventricle; and*

*a pulse generator, connected to the electrode, operative upon sensing of a ventricular depolarization signal from the right ventricle to apply a stimulating pulse to another ventricle.*

*85. The heart stimulating device of claim 84, wherein the pulse generator applies the stimulating pulse to the left ventricle.*

*86. The heart stimulating device of claim 84, wherein the pulse generator applies stimulating pulses to both the left ventricle and the right ventricle.*

*87. The heart stimulating device of claim 84, wherein the pulse generator applies the stimulating pulse immediately upon the sensing the ventricular depolarization signal.*

*88. The heart stimulating device of claim 84, further comprising:*

*a timer to initiate a delay period after the sensing of the ventricular depolarization signal.*

*89. The heart stimulating device of claim 88, wherein the pulse generator applies the stimulating pulse after the delay period.*

*90. A heart stimulating device for treating heart failure, comprising:*

*means for sensing ventricular depolarization signals originating from the right ventricle; and*

*means for applying a stimulating pulse to another ventricle in response to the sensing means sensing a ventricular depolarization signal originating from the right ventricle.*

*91. The heart stimulating device of claim 90, wherein the applying means applies the stimulating pulse to the left ventricle.*

*92. The heart stimulating device of claim 90, wherein the applying means applies stimulating pulses to both the left ventricle and the right ventricle.*

*93. The heart stimulating device of claim 90, wherein the applying means applies the stimulating pulse immediately upon the sensing of the ventricular depolarization signal.*

*94. The heart stimulating device of claim 90, further comprising:*

*means to initiate a delay period after the sensing of the ventricular depolarization signal.*

*95. The heart stimulating device of claim 94, wherein the applying means applies the stimulating pulse after the delay period.*

*96. A method for improving the hemodynamic efficiency of a heart, comprising:*

*sensing ventricular depolarization signals originating from the right ventricle; and*

*applying a stimulating pulse to another ventricle in response to the sensing of a ventricular depolarization signal originating from the right ventricle.*

*97. The method of claim 96, the applying further comprising:*

*applying the stimulating pulse to the left ventricle.*

*98. The method of claim 96, the applying further comprising:*

*applying stimulating pulses to both the left ventricle and the right ventricle.*

*99. The method of claim 96, the applying further comprising:*

*applying the stimulating pulse immediately upon the sensing of the ventricular depolarization signal.*

*100. The method of claim 96, further comprising:*

*initiating a delay period after the sensing of the ventricular depolarization signal.*

*101. The method of claim 100, the applying further comprising:*

*applying the stimulating pulse after the delay period.*

*102. A heart stimulating device for treating heart failure, comprising:*

*an electrode to sense ventricular depolarization signals originating from the right ventricle; and*

*a pulse generator operative upon sensing of a ventricular depolarization signal to apply a stimulating pulse to another ventricle.*

*103. The heart stimulating device of claim 102, wherein the pulse generator applies the stimulating pulse to the right ventricle.*

*104. The heart stimulating device of claim 102, wherein the pulse generator applies a stimulating pulse to both the right ventricle and the left ventricle.*

*105. The heart stimulating device of claim 102, wherein the pulse generator applies the stimulating pulse immediately upon the sensing of the ventricular depolarization signal.*

*106. The heart stimulating device of claim 102, further comprising:*

*a timer to initiate a delay period after the sensing of the ventricular depolarization signal.*

*107. The heart stimulating device of claim 106, wherein the pulse generator applies the stimulating pulse after the delay period.*

*108. A heart stimulating device for treating heart failure, comprising:*

*means for sensing ventricular depolarization signals originating from the left ventricle; and*

*means for applying a stimulating pulse to another ventricle in response to the sensing means sensing ventricular depolarization signals originating from the left ventricle.*

*109. The heart stimulating device of claim 108, wherein the applying means applies the stimulating pulse to the right ventricle.*

*110. The heart stimulating device of claim 108, wherein the applying means applies a stimulating pulse to both the right ventricle and the left ventricle.*

*111. The heart stimulating device of claim 108, wherein the applying means applies the stimulating pulse immediately upon the sensing of the ventricular depolarization signal.*

*112. The heart stimulating device of claim 108, further comprising:*

*means for initiating a delay period after the sensing of the ventricular depolarization signal.*

*113. The heart stimulating device of claim 112, wherein the applying means applies the stimulating pulse after the delay period.*

*114. A method for improving the hemodynamic efficiency of a heart, comprising:*

*sensing ventricular depolarization signals originating from the left ventricle; and*

*applying a stimulating pulse to another ventricle in response to the sensing of the ventricular depolarization signals originating from the left ventricle.*

*115. The method of claim 114, the applying further comprising:*

*applying the stimulating pulse to the right ventricle.*

*116. The method of claim 114, the applying further comprising:*

*applying a stimulating pulse to both the right ventricle and the left ventricle.*

*117. The method of claim 114, the applying further comprising:*

*applying the stimulating pulse immediately upon the sensing of the ventricular depolarization signal.*

*118. The method of claim 114, further comprising:*

*initiating a delay period after the sensing of the ventricular depolarization signal.*

*119. The method of claim 118, the applying further comprising:*

*applying the stimulating pulse after the delay period.*

*120. A heart stimulating device for treating heart failure, comprising:*

*a first electrode to sense atrial cardiac depolarization signals originating from an atrial chamber;*

*a second electrode to sense ventricular cardiac depolarization signals originating from a ventricular chamber;*

*a pulse generator operative to apply stimulating pulses to both ventricles in the event that no ventricular cardiac depolarization signals are sensed within a predetermined atrial-ventricular delay period.*

*121. The heart stimulating device of claim 120, further comprising:*

*a control circuit, connected to the first and second electrodes, to determine whether ventricular cardiac depolarization signals are sensed by the second electrode within the predetermined atrial-ventricular delay period.*

*122. The heart stimulating device of claim 120, wherein the pulse generator applies the stimulating pulses to both ventricles simultaneously.*

*123. The heart stimulating device of claim 120, wherein the pulse generator applies the stimulating pulses to each of the ventricles sequentially.*

*124. A heart stimulating device for treating heart failure, comprising:*

*means for sensing atrial cardiac depolarization signals originating from an atrial chamber;*

*means for sensing ventricular cardiac depolarization signals originating from a ventricular chamber;*

*means for applying stimulating pulses to both ventricles in the event that no ventricular cardiac depolarization signals are sensed within a predetermined atrial-ventricular delay period.*

*125. The heart stimulating device of claim 124, further comprising:*

*a control means, connected to the atrial sensing means and the ventricular sensing means, for determining whether ventricular cardiac depolarization signals are sensed by the ventricular sensing means within the predetermined atrial-ventricular delay period.*

*126. The heart stimulating device of claim 124, wherein the applying means applies the stimulating pulses to both ventricles simultaneously.*

*127. The heart stimulating device of claim 124, wherein the applying means applies the stimulating pulses to each of the ventricles sequentially.*

*128. A method for improving the hemodynamic efficiency of a heart, comprising:*

*sensing for the presence of cardiac depolarization signals from a ventricle; and*

*stimulating both ventricles in the event that no cardiac depolarization signals are sensed from either ventricle within a predetermined atrial-ventricular delay period.*

*129. The method of claim 128, wherein stimulating both ventricles further comprises generating a stimulating pulse and immediately and unconditionally applying the stimulating pulse to both ventricles.*

*130. The method of claim 128, wherein stimulating both ventricles further comprises generating a stimulating pulse and applying the stimulating pulse to both ventricles simultaneously.*

*131. The method of claim 128, wherein stimulating both ventricles further comprises generating a stimulating pulse and sequentially applying the stimulating pulse to the ventricles.*

*132. An atrial-coupled bi-ventricular stimulating device for treatment of congestive heart failure comprising:*

*atrial and ventricular sensing means for detecting cardiac signals originating in an atrium and in a ventricle;*

*a control circuit connected to said sensing means to receive the cardiac signals and provide a control signal; and*

*a stimulating circuit for effecting simultaneous contraction of both ventricles in response to the control signal of the control circuit after a predetermined A-V delay period.*

*133. An atrial-coupled bi-ventricular stimulating device for implantation or external use for treating heart failure comprising:*

*a sensing electrode adapted to be located in an atrium;*

*a pacing electrode adapted to be located through the coronary sinus in the left ventricle;*

*a sensing electrode adapted to be located in the right ventricle;*

*ventricular sensing means for detecting cardiac signals from the sensing electrode adapted to be in the right ventricle;*

*a control circuit connected to said sensing means to provide a control signal in response to detecting a cardiac signal; and*

*a stimulating circuit for effecting simultaneous contraction of both ventricles in response to the control signal of the control circuit after a predetermined A-V delay period.*

*134. The stimulating device of claim 133, wherein the sensing electrode adapted to be in the right ventricle also functions to deliver an electrical pulse from said stimulating circuit in response to the control signal of the control circuit.*

*135. The stimulating device of claim 133, wherein the pacing electrode delivers an electrical pulse from said stimulating circuit in response to the control signal of the control circuit.*

*136. A method for treating congestive heart failure comprising:*

*locating a sensing electrode in an atrium;*

*locating a pacing electrode through the coronary sinus in the left ventricle;*

*locating a sensing electrode in the right ventricle;*

*sensing for cardiac signals from the sensing electrode in the right ventricle;*

*detecting the cardiac signals; and*

*effecting simultaneous contraction of both ventricles after a predetermined A-V delay period.*

*137. The method of claim 136, wherein locating a sensing electrode in the right ventricle includes locating a sensing and pacing electrode in the right ventricle.*

*138. The method of claim 137, wherein effecting simultaneous contraction of both ventricles after a predetermined A-V delay period includes delivering an electrical pulse to the right ventricle via the sensing and pacing electrode.*

*139. The method of claim 136, wherein effecting simultaneous contraction of both ventricles after a predetermined A-V delay period includes delivering an electrical pulse to the left ventricle via the pacing electrode.*

*140. A method of effecting simultaneous contraction of both left and right ventricles of a heart for improving hemodynamic efficiency comprising:*

*locating a pacing electrode through the coronary sinus to the left ventricle;*

*sensing the cardiac signals of the atria and separately sensing the cardiac depolarization signals of the right ventricle;*

*detecting the cardiac signals of the atria and the cardiac depolarization signals of the right ventricle; and*

*stimulating the left ventricle simultaneously with the contraction of the right ventricle after a predetermined A-V delay period.*

*141. The method of claim 140, wherein stimulating the left ventricle simultaneously with the contraction of the right ventricle after a predetermined A-V delay period includes delivering an electrical pulse to the left ventricle via the pacing electrode.*

*142. The method of claim 140, wherein stimulating the left ventricle simultaneously with the contraction of the right ventricle after a predetermined A-V delay period includes stimulating both the left ventricle and the right ventricle after a predetermined A-V delay period.*

*143. A heart stimulating device for treating heart failure, comprising:*

*an electrode adapted to be disposed in or about the right ventricle to sense ventricular depolarization signals originating from the right ventricle;*

*a sense amplifier to receive the ventricular depolarization signals originating from the right ventricle;*

*a pulse generator, connected to the sense amplifier, to generate a stimulating pulse in the event the sense amplifier receives a ventricular depolarization signal originating from the right ventricle; and*

*an electrode, adapted to be disposed in or about the left ventricle and connected to the pulse generator, to apply*

*the stimulating pulse to the left ventricle in the event the sense amplifier receives a ventricular depolarization signal originating from the right ventricle.*

*144. The heart stimulating device of claim 143, wherein the electrode adapted to be disposed in or about the left ventricle is positioned through the coronary sinus.*

*145. The heart stimulating device of claim 143, wherein the electrode adapted to be disposed in or about the right ventricle stimulates the right ventricle in the event the sense amplifier receives a ventricular depolarization signal originating from the right ventricle.*

*146. A method for treating congestive heart failure, comprising:*

*receiving ventricular depolarization signals originating from the right ventricle;*

*generating a stimulating pulse in response to the receiving of a ventricular depolarization signal in the right ventricle; and*

*applying the stimulating pulse to the left ventricle in response to the receiving of a ventricular depolarization signal in the right ventricle.*

*147. The method of claim 146, the applying further comprising:*

*applying stimulating pulses to both the left ventricle and the right ventricle in response to the receiving of a ventricular depolarization signal in the right ventricle.*

*148. The method of claim 146, further comprising:*

*locating an electrode through the coronary sinus and in the left ventricle.*

*149. A heart stimulating device for treating heart failure, comprising:*

*an electrode adapted to be disposed in or about the left ventricle to sense ventricular depolarization signals originating from the left ventricle;*

*a sense amplifier to receive the ventricular depolarization signals originating from the left ventricle;*

*a pulse generator, connected to the sense amplifier, to generate a stimulating pulse in the event the sense amplifier receives a ventricular depolarization signal originating from the left ventricle; and*

*an electrode, adapted to be disposed in or about the right ventricle and connected to the pulse generator, to apply the stimulating pulse to the right ventricle in the event the sense amplifier receives a ventricular depolarization signal originating from the left ventricle.*

*150. The heart stimulating device of claim 149, wherein the electrode adapted to be disposed in or about the left ventricle is positioned through the coronary sinus.*

*151. The heart stimulating device of claim 149, wherein the electrode adapted to be disposed in or about the left ventricle stimulates the left ventricle in the event the sense amplifier receives a ventricular depolarization signal originating from the left ventricle.*

*152. A method for treating a heart suffering from heart failure, comprising:*

*receiving ventricular depolarization signals originating from the left ventricle;*

*generating a stimulating pulse in response to the receiving of a ventricular depolarization signal in the left ventricle; and*

*applying the stimulating pulse to the right ventricle in response to the receiving of a ventricular depolarization signal in the left ventricle.*

*153. The method of claim 152, the applying further comprising:*

*applying stimulating pulses to both the left ventricle and the right ventricle in response to the receiving of a ventricular depolarization signal in the left ventricle.*

*154. The method of claim 152, further comprising:*

*locating an electrode through the coronary sinus and in the left ventricle.*

*155. A method for improving the hemodynamic efficiency of a heart, comprising:*

*detecting a cardiac depolarization signal originating from a first ventricle; and*

*unconditionally stimulating both ventricles for effecting a coordinated contraction of both ventricles when a cardiac depolarization signal originating from the first ventricle is detected.*

*156. The method of claim 155, wherein unconditionally stimulating both ventricles includes providing electrical pulses from a stimulating circuit to both ventricles.*

*157. The method of claim 155, wherein detecting a cardiac depolarization signal further comprises conducting the signal to a sense amplifier to amplify the detected signal, and applying the amplified signal to a control circuit.*

*158. A heart stimulating device for treating heart failure, comprising:*

*an electrode adapted to be disposed in or about a first ventricle for detecting a cardiac depolarization signal originating from the first ventricle;*

*a sense amplifier to receive the cardiac depolarization signal originating from the first ventricle;*

*a pulse generator, connected to the sense amplifier, to unconditionally stimulate both ventricles for effecting a coordinated contraction of both ventricles when the cardiac depolarization signal from the first ventricle is detected.*

*159. The heart stimulating device of claim 158, further comprising an electrode adapted to be disposed in or about a second ventricle.*

*160. The heart stimulating device of claim 159, wherein the pulse generator unconditionally stimulates both ventricles by delivering an electronic pulse to the first ventricle via the electrode adapted to be disposed in or about the first ventricle and by delivering an electronic pulse to the second ventricle via the electrode adapted to be disposed in or about the second ventricle.*

*161. A method of improving the pumping ability of a heart suffering from heart failure comprising:*

*sensing for depolarization signals originating from a left ventricle;*

*sensing for depolarization signals originating from a right ventricle; and*

*stimulating the left ventricle and the right ventricle when a depolarization signal from either the left ventricle or the right ventricle is detected for effecting a coordinate contraction of ventricles contracting in an incoordinate manner to improve the pumping ability of the heart suffering from heart failure.*

*162. The method of claim 161, further comprising locating an electrode through the coronary sinus to the left ventricle.*

*163. The method of claim 162, further comprising locating an electrode in the right ventricle.*

*164. The method of claim 161, wherein stimulating the left ventricle and the right ventricle includes stimulating the left ventricle and the right ventricle within a period of time after detecting a depolarization signal from either the left ventricle or the right ventricle, the period of time being sufficient to effect a substantially simultaneous contraction of the ventricles.*

*165. The method of claim 164, wherein the left ventricle and the right ventricle are stimulated within 10 milliseconds after detecting the depolarization signal.*

*166. The method of claim 161, wherein stimulating the left ventricle and the right ventricle includes stimulating only one site in the left ventricle and only one site in the right ventricle.*

*167. The method of claim 161, wherein stimulating the left ventricle and the right ventricle includes stimulating the left ventricle and the right ventricle when a depolarization signal from either the left ventricle or the right ventricle is detected regardless of whether both ventricles would otherwise contract substantially simultaneously.*

*168. The method of claim 161, wherein stimulating the left ventricle and the right ventricle includes applying a pacing pulse to the left ventricle and applying a pacing pulse to the right ventricle.*

*169. The method of claim 161, wherein stimulating the left ventricle and the right ventricle includes stimulating the left ventricle substantially simultaneously with stimulating the right ventricle.*

*170. The method of claim 161, further comprising stimulating the left ventricle and the right ventricle if a depolarization signal from either the left ventricle or the right ventricle is not detected within a period of time.*

*171. A method of improving the pumping ability of a heart suffering from heart failure comprising:*

*sensing for depolarization signals only from one ventricle of the heart;*

*stimulating the left ventricle and the right ventricle when a depolarization signal from the one ventricle is detected for effecting a coordinate contraction of ventricles contracting in an incoordinate manner to improve the pumping ability of the heart suffering from heart failure.*

*172. The method of claim 171, further comprising locating an electrode through the coronary sinus to the left ventricle.*

*173. The method of claim 172, further comprising locating an electrode in the right ventricle.*

*174. The method of claim 171, wherein stimulating the left ventricle and the right ventricle includes stimulating the left ventricle and the right ventricle within a period of time after detecting a depolarization signal from the one ventricle, the period of time being sufficient to effect a substantially simultaneous contraction of the ventricles.*

*175. The method of claim 174, wherein the left ventricle and the right ventricle are stimulated within 10 milliseconds after detecting the depolarization signal.*

*176. The method of claim 171, wherein stimulating the left ventricle and the right ventricle includes stimulating only one site in the left ventricle and only one site in the right ventricle.*

*177. The method of claim 171, wherein stimulating the left ventricle and the right ventricle includes stimulating the left ventricle and the right ventricle when a depolarization signal from the one ventricle is detected regardless of whether both ventricles would otherwise contract substantially simultaneously.*

*178. The method of claim 171, wherein stimulating the left ventricle and the right ventricle includes applying a pacing pulse to the left ventricle and applying a pacing pulse to the right ventricle.*

*179. The method of claim 171, wherein stimulating the left ventricle and the right ventricle includes stimulating the left ventricle substantially simultaneously with stimulating the right ventricle.*

*180. The method of claim 171, further comprising stimulating the left ventricle and the right ventricle if a depolarization signal from the one ventricle is not detected within a period of time.*

*181. The method of claim 171, wherein the one ventricle is the right ventricle.*

*182. The method of claim 171, wherein the one ventricle is the left ventricle.*

*183. A heart failure treatment device for improving the pumping ability of a heart suffering from heart failure comprising:*

*a sense amplifier for receiving depolarization signals originating from left and right ventricles; and*

*a pulse generator, connected to the sense amplifier, that generates stimulation pulses for application to the left ventricle and the right ventricle when the sense amplifier receives a ventricular depolarization signal originating from either the left ventricle or the right ventricle for effecting a coordinated contraction of the ventricles to improve the pumping ability of the heart suffering from heart failure;*

*a first electrode connected to the pulse generator and adapted to be disposed in or about the left ventricle for sensing depolarization signals originating from the left ventricle and for applying a stimulation pulse to the left ventricle when the sense amplifier receives a ventricular depolarization signal originating from either the left ventricle or the right ventricle; and*

*a second electrode connected to the pulse generator and adapted to be disposed in or about the right ventricle for sensing depolarization signals originating from the right ventricle and for applying a stimulation pulse to the right ventricle when the sense amplifier receives a ventricular depolarization signal originating from either the left ventricle or the right ventricle.*

*184. The heart failure treatment device of claim 183, wherein the first electrode is adapted to be positioned through the coronary sinus to the left ventricle.*

*185. The heart failure treatment device of claim 183, wherein the stimulation pulse is applied to the left ventricle and the stimulation pulse applied to the right ventricle within a period of time after the sense amplifier receives a depolarization signal originating from the left ventricle or the right ventricle, the period of time being sufficient to effect substantially simultaneous contraction of the left and right ventricles.*

*186. The heart failure treatment device of claim 185, wherein the stimulation pulse is applied to the left ventricle and the stimulation pulse applied to the right ventricle within 10 milliseconds after the sense amplifier receives a depolarization signal originating from the left ventricle or the right ventricle.*

*187. The heart failure treatment device of claim 183, wherein the pulse generator generates stimulation pulses for application to the left ventricle and the right ventricle when the sense amplifier receives a ventricular depolarization signal originating from either the left ventricle or the right ventricle regardless of whether both ventricles would otherwise contract substantially simultaneously.*

*188. The heart failure treatment device of claim 183, wherein the stimulation pulses generated by the pulse generator are pacing pulses.*

*189. The heart failure treatment device of claim 183, wherein the stimulation pulse applied to the left ventricle is applied substantially simultaneously with the stimulation pulse applied to the right ventricle.*

*190. The heart failure treatment device of claim 183, wherein the sense amplifier includes a first sense amplifier*

*for receiving depolarization signals originating from the right ventricle and a second sense amplifier for receiving depolarization signals from the left ventricle.*

*191. The heart failure treatment device of claim 183, wherein the pulse generator generates stimulation pulses for application to the left ventricle and the right ventricle if a depolarization signal originating from either the left ventricle or the right ventricle is not detected within a period of time.*

*192. A heart failure treatment device for improving the pumping ability of a heart suffering from heart failure comprising:*

*a sense amplifier for receiving depolarization signals originating from a left ventricle or a right ventricle;*

*a pulse generator, connected to the sense amplifier, that generates stimulation pulses for application to the left ventricle and the right ventricle when the sense amplifier receives a ventricular depolarization signal originating from the left ventricle or the right ventricle for effecting a coordinated contraction of the ventricles to improve the pumping ability of the heart suffering from heart failure;*

*a first electrode connected to the pulse generator and adapted to be disposed in or about the left ventricle, the first electrode capable of sensing depolarization signals originating from the left ventricle and capable of applying a stimulation pulse to the left ventricle when the sense amplifier receives a ventricular depolarization signal originating from the left ventricle or the right ventricle; and*

*a second electrode connected to the pulse generator and adapted to be disposed in or about the right ventricle, the second electrode capable of sensing depolarization signals originating from the right ventricle and capable of applying a stimulation pulse to the right ventricle when the sense amplifier receives a ventricular depolarization signal originating from the left ventricle or the right ventricle.*

*193. The heart failure treatment device of claim 192, wherein the first electrode is adapted to be positioned through the coronary sinus to the left ventricle.*

*194. The heart failure treatment device of claim 192, wherein the stimulation pulse is applied to the left ventricle and the stimulation pulse applied to the right ventricle within a period of time after the sense amplifier receives a depolarization signal originating from the left ventricle or the right ventricle, the period of time being sufficient to effect substantially simultaneous contraction of the left and right ventricles.*

*195. The heart failure treatment device of claim 194, wherein the stimulation pulse is applied to the left ventricle and the stimulation pulse applied to the right ventricle within 10 milliseconds after the sense amplifier receives a depolarization signal originating from the left ventricle or the right ventricle.*

*196. The heart failure treatment device of claim 192, wherein the pulse generator generates stimulation pulses for application to the left ventricle and the right ventricle when the sense amplifier receives a ventricular depolarization signal originating from the left ventricle or the right ventricle regardless of whether both ventricles would otherwise contract substantially simultaneously.*

*197. The heart failure treatment device of claim 192, wherein the stimulation pulses generated by the pulse generator are pacing pulses.*

*198. The heart failure treatment device of claim 192, wherein the stimulation pulse applied to the left ventricle is applied substantially simultaneously with the stimulation pulse applied to the right ventricle.*

*199. The heart failure treatment device of claim 192, wherein the pulse generator generates stimulation pulses for application to the left ventricle and the right ventricle if a depolarization signal from the left ventricle or the right ventricle is not detected within a period of time.*

*200. A heart failure treatment device for improving the pumping ability of a heart suffering from heart failure comprising:*

*a sense amplifier for receiving depolarization signals originating from only one ventricle of the heart;*

*a pulse generator, connected to the amplifier for generating stimulation pulses for application to the left ventricle and the right ventricle when the sense amplifier receives a ventricular depolarization signal originating from the one ventricle for effecting a coordinated contraction of the ventricles to improve the pumping ability of the heart suffering from heart failure;*

*a first electrode connected to the pulse generator and adapted to be disposed in or about the left ventricle for applying a stimulation pulse to the left ventricle when the sense amplifier receives a ventricular depolarization signal originating from the one ventricle; and*

*a second electrode connected to the pulse generator and adapted to be disposed in or about the right ventricle for applying a stimulation pulse to the right ventricle when the sense amplifier receives a ventricular depolarization signal originating from the one ventricle.*

*201. The heart failure treatment device of claim 200, wherein the first electrode is adapted to be positioned through the coronary sinus to the left ventricle.*

*202. The heart failure treatment device of claim 200, wherein the stimulation pulse is applied to the left ventricle and the stimulation pulse applied to the right ventricle within a period of time after the sense amplifier receives a depolarization signal originating from the one ventricle, the period of time being sufficient to effect substantially simultaneous contraction of the left and right ventricles.*

*203. The heart failure treatment device of claim 202, wherein the stimulation pulse is applied to the left ventricle and the stimulation pulse applied to the right ventricle within 10 milliseconds after the sense amplifier receives a depolarization signal originating from the one ventricle.*

*204. The heart failure treatment device of claim 200, wherein the pulse generator generates stimulation pulses for application to the left ventricle and the right ventricle when the sense amplifier receives a ventricular depolarization signal originating from the one ventricle regardless of whether both ventricles would otherwise contract substantially simultaneously.*

*205. The heart failure treatment device of claim 200, wherein the stimulation pulses generated by the pulse generator are pacing pulses.*

*206. The heart failure treatment device of claim 200, wherein the stimulation pulse applied to the left ventricle is applied substantially simultaneously with the stimulation pulse applied to the right ventricle.*

*207. The heart failure treatment device of claim 200, wherein the one ventricle is the right ventricle.*

*208. The heart failure treatment device of claim 200, wherein the one ventricle is the left ventricle.*

*209. The heart failure treatment device of claim 200, wherein the pulse generator generates stimulation pulses for application to the left ventricle and the right ventricle if a depolarization signal from the one ventricle is not detected within a period of time.*

*210. A method for improving the pumping ability of a heart suffering from heart failure comprising:*

*sensing for depolarization signals originating from an atrium;*

*beginning an atrial-ventricular delay period upon sensing a depolarization signal of the atrium;*

*sensing for depolarization signals originating from a left ventricle;*

*sensing for depolarization signals originating from a right ventricle; and*

*stimulating the left ventricle and the right ventricle at the end of the atrial-ventricular delay period if a depolarization signal is not detected from either the left ventricle or the right ventricle during the atrial-ventricular delay period for effecting a coordinated contraction of ventricles contracting in an incoordinate manner to improve the pumping ability to the heart suffering form heart failure.*

*211. The method of claim 210, further comprising locating an electrode through the coronary sinus to the left ventricle.*

*212. The method of claim 211, further comprising locating an electrode in the right ventricle.*

*213. The method of claim 210, wherein stimulating the left ventricle and the right ventricle includes stimulating only one site in the left ventricle and only one site in the right ventricle.*

*214. The method of claim 210, wherein stimulating the left ventricle and the right ventricle includes applying a pacing pulse to the left ventricle and applying a pacing pulse to the right ventricle.*

*215. The method of claim 210, wherein stimulating the left ventricle and the right ventricle includes stimulating the left ventricle substantially simultaneously with stimulating the right ventricle.*

*216. A method for improving the pumping ability of a heart suffering from heart failure comprising:*

*sensing for depolarization signals originating from an atrium;*

*beginning an atrial-ventricular delay period upon sensing a depolarization signal of the atrium;*

*sensing for depolarization signals originating from only one ventricle; and*

*stimulating the left ventricle and the right ventricle at the end of the atrial-ventricular delay period if a depolarization signal is not detected from the one ventricle during the atrial-ventricular delay period for effecting a coordinated contraction of ventricles contracting in an incoordinate manner to improve the pumping ability to the heart suffering form heart failure.*

*217. The method of claim 216, further comprising locating an electrode through the coronary sinus to the left ventricle.*

*218. The method of claim 217, further comprising locating an electrode in the right ventricle.*

*219. The method of claim 216, wherein stimulating the left ventricle and the right ventricle includes stimulating only one site in the left ventricle and only one site in the right ventricle.*

*220. The method of claim 216, wherein stimulating the left ventricle and the right ventricle includes applying a pacing pulse to the left ventricle and applying a pacing pulse to the right ventricle.*

*221. The method of claim 216, wherein stimulating the left ventricle and the right ventricle includes stimulating the left ventricle substantially simultaneously with stimulating the right ventricle.*

*222. The method of claim 216, wherein the one ventricle is the right ventricle.*

*223. The method of claim 216, wherein the one ventricle is the left ventricle.*

*224. A heart failure treatment device for improving the pumping ability of a heart suffering from heart failure comprising:*

*an atrial sense amplifier for detecting depolarization signals originating from an atrium;*

*a ventricular sense amplifier for detecting depolarization signals originating from a left ventricle and a right ventricle;*

*pacing control circuitry, connected to the atrial sense amplifier, for starting an atrial-ventricular delay period when the atrial sense amplifier detects an atrial depolarization signal; and*

*a stimulating circuit capable of stimulating the left ventricle and the right ventricle at the end of the atrial-ventricular delay period if a depolarization signal is not detected from either the left ventricle or the right ventricle during the atrial-ventricular delay period for effecting coordinated contraction of ventricles contracting in an incoordinate manner to improve the pumping ability to the heart suffering form heart failure.*

*225. The heart failure treatment device of claim 224, further comprising an electrode adapted to be positioned through the coronary sinus to the left ventricle for stimulating the left ventricle.*

*226. The heart failure treatment device of claim 224, wherein the stimulating circuit generates pacing pulses for stimulating the left ventricle and the right ventricle.*

*227. The heart failure treatment device of claim 224, wherein the stimulation circuit stimulates the left ventricle substantially simultaneously with stimulation of the right ventricle.*

*228. The heart failure treatment device of claim 224, wherein the ventricular sense amplifiers includes a first ventricular sense amplifier connected to the pacing control circuitry for detecting depolarization signals originating from the left ventricle and a second ventricular sense amplifier connected to the pacing control circuitry for detecting depolarization signals originating from the right ventricle.*

*229. A heart failure treatment device for improving the pumping ability of a heart suffering from heart failure comprising:*

*an atrial sense amplifier capable of detecting depolarization signals originating from an atrium;*

*a ventricular sense amplifier capable of detecting depolarization signals originating from a left ventricle or a right ventricle;*

*pacing control circuitry, connected to the atrial sense amplifier, capable of starting an atrial-ventricular delay period when the atrial sense amplifier detects an atrial depolarization signal;*

*a stimulating circuit capable of providing stimulating pulses for application to the left ventricle and the right ventricle at the end of the atrial-ventricular delay period if a depolarization signal is not detected from the left ventricle or the right ventricle during the atrial-ventricular delay period for effecting coordinated contraction of ventricles contracting in an incoordinate manner to improve the pumping ability to the heart suffering form heart failure;*

*a first electrode responsive to the stimulating circuit and adapted to be disposed in or about the left ventricle, the*

*first electrode capable of sensing depolarization signals originating from the left ventricle and capable of providing stimulating pulses to the left ventricle when the ventricular sense amplifier receives a depolarization signal from the left ventricle or the right ventricle; and*

*a second electrode responsive to the stimulating circuit and adapted to be disposed in or about the right ventricle, the second electrode capable of sensing depolarization signals originating from the right ventricle and capable of providing stimulating pulses to the right ventricle when the sense amplifier receives a depolarization signal from the left ventricle or the right ventricle.*

*230. The heart failure treatment device of claim 229, wherein the first electrode is adapted to be positioned through the coronary sinus to the left ventricle.*

*231. The heart failure treatment device of claim 229, wherein the left ventricle is stimulated substantially simultaneously with stimulation of the right ventricle.*

*232. A heart failure treatment device for improving the pumping ability of a heart suffering from heart failure comprising:*

*an atrial sense amplifier for detecting depolarization signals originating from an atrium;*

*a ventricular sense amplifier for detecting depolarization signals originating from only one ventricle;*

*pacing control circuitry, connected to the atrial sense amplifier, for starting an atrial-ventricular delay period when the atrial sense amplifier detects an atrial depolarization signal; and*

*a stimulating circuit capable of stimulating the left ventricle and the right ventricle at the end of the atrial-ventricular delay if a depolarization signal is not detected from the one ventricle during the atrial-ventricular delay period for effecting coordinated contraction of ventricles contracting in an incoordinate manner to improve the pumping ability to the heart suffering form heart failure.*

*233. The heart failure treatment device of claim 232, further comprising an electrode adapted to be positioned through the coronary sinus to the left ventricle for stimulating the left ventricle.*

*234. The heart failure treatment device of claim 232, wherein the stimulating circuit generates pacing pulses for stimulating the left ventricle and the right ventricle.*

*235. The heart failure treatment device of claim 232, wherein the stimulation circuit stimulates the left ventricle substantially simultaneously with stimulation of the right ventricle.*

*236. The heart failure treatment device of claim 232, wherein the one ventricle is the right ventricle.*

*237. The heart failure treatment device of claim 232, wherein the one ventricle is the left ventricle.*

*238. A method of improving the pumping ability of a heart suffering from heart failure comprising:*

*sensing for depolarization signals originating from an atrium;*

*beginning an atrial-ventricular delay period upon sensing a depolarization signal of the atrium;*

*sensing for depolarization signals originating from a left ventricle;*

*sensing for depolarization signals originating from a right ventricle; and*

*stimulating the left ventricle and the right ventricle when a depolarization signal from either the left ventricle or the right ventricle is detected during the atrial-ventricular delay period for effecting a coordinated contraction of the ventricles contracting in an incoordinate manner to improve the pumping ability of the heart suffering from heart failure; and*

*stimulating the left ventricle and the right ventricle at the end of the atrial-ventricular delay period if a depolarization signal is not detected from either the left ventricle or the right ventricle during the atrial-ventricular delay period for effecting a coordinated contraction of the ventricles.*

*239. The method of claim 238, further comprising locating an electrode through the coronary sinus to the left ventricle.*

*240. The method of claim 239, further comprising locating an electrode in the right ventricle.*

*241. The method of claim 238, wherein the left ventricle is stimulated and the right ventricle is stimulated within a period of time after a depolarization signal from either the left ventricle or the right ventricle is detected during the atrial-ventricular delay period, the period of time being sufficient for effecting substantially simultaneous contraction of the ventricles.*

*242. The method of claim 241, wherein the left ventricle and the right ventricle are stimulated within 10 milliseconds of the detection of the depolarization signal.*

*243. The method of claim 238, wherein stimulating the left ventricle and the right ventricle includes stimulating only one site in the left ventricle and only one site in the right ventricle.*

*244. The method of claim 238, wherein the left ventricle and the right ventricle are stimulated when a depolarization signal from either the left ventricle or the right ventricle is detected during the atrial-ventricular delay period regardless of whether both ventricles would otherwise contract substantially simultaneously.*

*245. The method of claim 238, wherein stimulating the left ventricle and the right ventricle includes applying a pacing pulse to the left ventricle and applying a pacing pulse to the right ventricle.*

*246. The method of claim 238, wherein stimulating the left ventricle and the right ventricle includes stimulating the left ventricle substantially simultaneously with stimulating the right ventricle.*

*247. A method of improving the pumping ability of a heart suffering from heart failure comprising:*

*sensing for depolarization signals originating from an atrium;*

*beginning an atrial-ventricular delay period upon sensing a depolarization signal of the atrium;*

*sensing for depolarization signals originating from only one ventricle;*

*stimulating the left ventricle and the right ventricle when a depolarization signal from the one ventricle is detected during the atrial-ventricular delay period for effecting a coordinated contraction of the ventricles; and*

*stimulating the left ventricle and the right ventricle at the end of the atrial-ventricular delay period if a depolarization signal is not detected from the one ventricle during the atrial-ventricular delay period for effecting a coordinated contraction of ventricles contracting in an incoordinate manner to improve the pumping ability of the heart suffering from heart failure.*

*248. The method of claim 247, further comprising locating an electrode through the coronary sinus to the left ventricle.*

*249. The method of claim 248, further comprising locating an electrode in the right ventricle.*

*250. The method of claim 247, wherein the left ventricle is stimulated and the right ventricle is stimulated within a period of time after a depolarization signal from the one depolarization is detected during the atrial-ventricular delay period, the period of time being sufficient for effecting substantially simultaneous contraction of the ventricles.*

*251. The method of claim 250, wherein the left ventricle and the right ventricle are stimulated within 10 milliseconds of the detection of the depolarization signal.*

*252. The method of claim 247, wherein stimulating the left ventricle and the right ventricle includes stimulating only one site in the left ventricle and only one site in the right ventricle.*

*253. The method of claim 247, wherein the left ventricle and the right ventricle are stimulated when a depolarization signal from the one ventricle is detected during the atrial-ventricular delay period regardless of whether both ventricles would otherwise contract substantially simultaneously.*

*254. The method of claim 247, wherein stimulating the left ventricle and the right ventricle includes applying a pacing pulse to the left ventricle and applying a pacing pulse to the right ventricle.*

*255. The method of claim 247, wherein stimulating the left ventricle and the right ventricle includes stimulating the left ventricle substantially simultaneously with stimulating the right ventricle.*

*256. The method of claim 247, wherein the one ventricle is the right ventricle.*

*257. The method of claim 247, wherein the one ventricle is the left ventricle.*

*258. A heart failure treatment device for improving the pumping ability of a heart suffering from heart failure comprising:*

*an atrial sense amplifier for detecting depolarization signals originating from an atrium;*

*pacing control circuitry, connected to the atrial sense amplifier, for starting an atrial-ventricular delay period when the atrial sense amplifier detects an atrial depolarization signal;*

*a ventricular sense amplifier for detecting depolarization signals originating from a left ventricle and a right ventricle; and*

*a stimulating circuit for stimulating the left ventricle and the right ventricle when a depolarization signal from either the left or the right ventricle is detected by the ventricular sense amplifier during the atrial-ventricular delay period for effecting a coordinated contraction of ventricles contracting in an incoordinate manner to improve the pumping ability of the heart suffering from heart failure; and for stimulating the left ventricle and the right ventricle at the end of the atrial-ventricular delay period if a depolarization signal is not detected from either the left or right ventricles during the atrial-ventricular delay period for effecting a coordinated contraction of ventricles contracting in an incoordinate manner to improve the pumping ability of the heart suffering from heart failure.*

*259. The heart failure treatment device of claim 259, further comprising an electrode adapted to be positioned through the coronary sinus to the left ventricle for stimulating the left ventricle.*

*260. The heart failure treatment device of claim 258, wherein the stimulation circuit stimulates the left ventricle and the right ventricle within a time period after a depolarization signal from either the left or the right ventricle is detected by the ventricular sense amplifier, the time period being sufficient for effecting substantially simultaneous contraction of the left ventricle and the right ventricle.*

*261. The heart failure treatment device of claim 260, wherein the stimulation circuit stimulates the left ventricle and the right ventricle within 10 milliseconds of the ventricular sense amplifier detecting a depolarization signal from either the left ventricle or the right ventricle.*

*262. The heart failure treatment device of claim 258, wherein the stimulating circuit stimulates the left ventricle and the right ventricle when a depolarization signal from either the left ventricle or the right ventricle is detected by the ventricular sense amplifier during the atrial-ventricular delay period regardless of whether both ventricles would otherwise contract substantially simultaneously.*

*263. The heart failure treatment device of claim 258, wherein the stimulating circuit generates pacing pulses for stimulating the left ventricle and the right ventricle.*

*264. The heart failure treatment device of claim 258, wherein the stimulation circuit stimulates the left ventricle substantially simultaneously with stimulation of the right ventricle.*

*265. The heart failure treatment device of claim 258, wherein the ventricular sense amplifiers includes a first ventricular sense amplifier for detecting depolarization signals originating from the left ventricle and second ventricular sense amplifier for detecting depolarization signals originating from the right ventricle.*

*266. A heart failure treatment device for improving the pumping ability of a heart suffering from heart failure comprising:*

*a atrial sense amplifier for detecting depolarization signals originating from an atrium;*

*pacing control circuitry, connected to the atrial sense amplifier, for starting an atrial-ventricular delay period when the atrial sense amplifier detects an atrial depolarization signal;*

*a ventricular sense amplifier for detecting depolarization signals originating from the left ventricle or the right ventricle;*

*a stimulating circuit for stimulating the left ventricle and the right ventricle when a depolarization signal from the left ventricle or the right ventricle is detected by the ventricular sense amplifier during the atrial-ventricular delay period for effecting a coordinated contraction of ventricles contracting in an incoordinate manner to improve the pumping ability of the heart suffering from heart failure; and for stimulating the left ventricle and the right ventricle at the end of the atrial-ventricular delay period if a depolarization signal is not detected from the left ventricle or the right ventricle during the atrial-ventricular delay period for effecting a coordinated contraction of ventricles contracting in an incoordinate manner to improve the pumping ability of the heart suffering from heart failure;*

*a first electrode adapted to be disposed in or about the left ventricle, the first electrode capable of sensing depolarization signals originating from the left ventricle and capable of providing a stimulating pulse to the left ventricle in response to the stimulating circuit; and*

*a second electrode adapted to be disposed in or about the right ventricle, the second electrode capable of sensing depolarization signals originating from the right ventricle and capable of providing a stimulating pulse to the right ventricle in response to the stimulating circuit.*

*267. The heart failure treatment device of claim 266, wherein the first electrode is adapted to be positioned through the coronary sinus to the left ventricle.*

*268. The heart failure treatment device of claim 266, wherein the stimulating circuit generates pacing pulses for stimulating the left ventricle and the right ventricle.*

*269. The heart failure treatment device of claim 266, wherein the left ventricle is stimulated substantially simultaneously with stimulation of the right ventricle.*

*270. The heart failure treatment device of claim 266, wherein the stimulation circuit stimulates the left ventricle and the right ventricle within a time period after a depolarization signal from the left ventricle or the right ventricle is detected by the ventricular sense amplifier, the time period being sufficient for effecting substantially simultaneous contraction of the left ventricle and the right ventricle.*

*271. The heart failure treatment device of claim 270, wherein the stimulation circuit stimulates the left ventricle and the right ventricle within 10 milliseconds of the ventricular sense amplifier detecting a depolarization signal from the left ventricle or the right ventricle.*

*272. A heart failure treatment device for improving the pumping ability of a heart suffering from heart failure comprising:*

*an atrial sense amplifier for detecting depolarization signals originating from an atrium;*

*pacing control circuitry, connected to the atrial sense amplifier, for starting an atrial-ventricular delay period when the atrial sense amplifier detects an atrial depolarization signal;*

*a ventricular sense amplifier for detecting depolarization signals originating from only one ventricle; and*

*a stimulating circuit for stimulating the left ventricle and the right ventricle when a depolarization signal from the one ventricle is detected by the ventricular sense amplifier during the atrial-ventricular delay period for effecting a coordinated contraction of ventricles contracting in an incoordinate manner to improve the pumping ability of the heart suffering from heart failure; and for stimulating the left ventricle and the right ventricle at the end of the atrial-ventricular delay period if a depolarization signal is not detected from the one ventricle during the atrial-ventricular delay period for effecting a coordinated contraction of ventricles contracting in an incoordinate manner to improve the pumping ability of the heart suffering from heart failure.*

*273. The heart failure treatment device of claim 272, further comprising an electrode adapted to be positioned through the coronary sinus to the left ventricle for stimulating the left ventricle.*

*274. The heart failure treatment device of claim 272, wherein the stimulation circuit stimulates the left ventricle and the right ventricle within a time period after a depolarization signal from the one ventricle is detected by the ventricular sense amplifier, the time period being sufficient for effecting substantially simultaneous contraction of the left ventricle and the right ventricle.*

*275. The heart failure treatment device of claim 274, wherein the stimulation circuit stimulates the left ventricle and the right ventricle within 10 milliseconds of the ventricular sense amplifier detecting a depolarization signal from the one ventricle.*

*276. The heart failure treatment device of claim 272, wherein the stimulating circuit stimulates the left ventricle and the right ventricle when a depolarization signal from the one ventricle is detected by the ventricular sense amplifier during the atrial-ventricular delay period regardless of whether both ventricles would otherwise contract substantially simultaneously.*

*277. The heart failure treatment device of claim 272, wherein the stimulating circuit generates pacing pulses for stimulating the left ventricle and the right ventricle.*

*278. The heart failure treatment device of claim 272, wherein the stimulation circuit stimulates the left ventricle substantially simultaneously with the stimulation of the right ventricle.*

*279. The heart failure treatment device of claim 272, wherein the one ventricle is the right ventricle.*

*280. The heart failure treatment device of claim 272, wherein the one ventricle is the left ventricle.*

*281. A method of improving the pumping ability of a heart suffering from heart failure comprising:*

*sensing for depolarization signals originating from an atrium;*

*beginning an atrial-ventricular delay period upon sensing a depolarization signal of the atrium;*

*sensing for depolarization signals originating from a left ventricle;*

*sensing for depolarization signals originating from a right ventricle;*

*inhibiting stimulation of the left ventricle and the right ventricle when a depolarization signal from either the left ventricle or the right ventricle is detected during the atrial-ventricular delay period; and*

*stimulating the left ventricle and the right ventricle at the end of the atrial-ventricular delay period if a depolarization signal is not detected from either the left ventricle or the right ventricle during the atrial-ventricular delay period.*

*282. The method of claim 281, further comprising locating an electrode through the coronary sinus to the left ventricle.*

*283. The method of claim 282, further comprising locating an electrode in the right ventricle.*

*284. The method of claim 281, wherein stimulating the left ventricle and the right ventricle includes stimulating only one site in the left ventricle and only one site in the right ventricle.*

*285. The method of claim 281, wherein stimulating the left ventricle and the right ventricle includes applying a pacing pulse to the left ventricle and applying a pacing pulse to the right ventricle.*

*286. The method of claim 281, wherein stimulating the left ventricle and the right ventricle includes stimulating the left ventricle substantially simultaneously with stimulating the right ventricle.*

*287. A method of improving the pumping ability of a heart suffering from heart failure comprising:*

*sensing for depolarization signals originating from an atrium;*

*beginning an atrial-ventricular delay period upon sensing a depolarization signal of the atrium;*

*sensing for depolarization signals originating from only one ventricle;*

*inhibiting stimulation of the left ventricle and the right ventricle when a depolarization signal from the one ventricle is detected during the atrial-ventricular delay period; and*

*stimulating the left ventricle and the right ventricle at the end of the atrial-ventricular delay period if a depolarization signal is not detected from the one ventricle during the atrial-ventricular delay period.*

*288. The method of claim 287, further comprising locating an electrode through the coronary sinus to the left ventricle.*

*289. The method of claim 288, further comprising locating an electrode in the right ventricle.*

*290. The method of claim 287, wherein stimulating the left ventricle and the right ventricle includes stimulating only one site in the left ventricle and only one site in the right ventricle.*

*291. The method of claim 287, wherein stimulating the left ventricle and the right ventricle includes applying a pacing pulse to the left ventricle and applying a pacing pulse to the right ventricle.*

*292. The method of claim 287, wherein stimulating the left ventricle and the right ventricle includes stimulating the left ventricle substantially simultaneously with stimulating the right ventricle.*

*293. A heart failure treatment device for improving the pumping ability of a heart suffering from heart failure comprising:*

*an atrial sense amplifier for detecting depolarization signals originating from an atrium;*

*a ventricular sense amplifier for detecting depolarization signals originating from a left ventricle and a right ventricle;*

*pacing control circuitry, connected to the atrial sense amplifier, for starting an atrial-ventricular delay period when the atrial sense amplifier detects an atrial depolarization signal, and for inhibiting stimulation of the left ventricle and the right ventricle when a depolarization signal from either the left or the right ventricle is detected during the atrial-ventricular delay period; and*

*a stimulating circuit for stimulating the left ventricle and the right ventricle at the end of the atrial-ventricular delay period if a depolarization signal is not detected from either the left ventricle or the right ventricle during the atrial-ventricular delay period for effecting a coordinated contraction of ventricles contracting in an incoordinate manner to improve the pumping ability of the heart suffering from heart failure.*

*294. The heart failure treatment device of claim 293, further comprising an electrode adapted to be positioned through the coronary sinus to the left ventricle for stimulating the left ventricle.*

*295. The heart failure treatment device of claim 293, wherein the stimulating circuit generates pacing pulses for stimulating the left ventricle and the right ventricle.*

*296. The heart failure treatment device of claim 293, wherein the stimulation circuit stimulates the left ventricle substantially simultaneously with the stimulation of the right ventricle.*

*297. The heart failure treatment device of claim 293, wherein the ventricular sense amplifier includes a first ventricular sense amplifier for receiving depolarization signals originating from the right ventricle and a second ventricular sense amplifier for receiving depolarization signals from the left ventricle.*

*298. A heart failure treatment device for improving the pumping ability of a heart suffering from heart failure comprising:*

*an atrial sense amplifier for detecting depolarization signals originating from an atrium;*

*a ventricular sense amplifier for detecting depolarization signals originating from a left ventricle or a right ventricle;*

*pacing control circuitry, connected to the atrial sense amplifier, for starting an atrial-ventricular delay period when the atrial sense amplifier detects an atrial depolarization signal, and for inhibiting stimulation of the left ventricle and the right ventricle when a depolarization signal from either the left or the right ventricle is detected during the atrial-ventricular delay period;*

*a stimulating circuit for providing stimulating pulses for application to the left ventricle and the right ventricle at the end of the atrial-ventricular delay period if a depolarization signal is not detected from the left ventricle or the right ventricle during the atrial-ventricular delay period for effecting a coordinated contraction of ventricles contracting in an incoordinate manner to improve the pumping ability of the heart suffering from heart failure;*

*a first electrode adapted to be disposed in or about the left ventricle, the first electrode capable of sensing depolarization signals originating from the left ventricle and capable of providing a stimulating pulse to the left ventricle in response to the stimulating circuit; and*

*a second electrode adapted to be disposed in or about the right ventricle, the second electrode capable of sensing depolarization signals originating from the right ventricle and capable of providing a stimulating pulse to the right ventricle in response to the stimulating circuit.*

*299. The heart failure treatment device of claim 298, wherein the first electrode is adapted to be positioned through the coronary sinus to the left ventricle.*

*300. The heart failure treatment device of claim 298, wherein the stimulating circuit generates pacing pulses for stimulating the left ventricle and the right ventricle.*

*301. The heart failure treatment device of claim 298, wherein the left ventricle is stimulated substantially simultaneously with the stimulation of the right ventricle.*

*302. A heart failure treatment device for improving the pumping ability of a heart suffering from heart failure comprising:*

*an atrial sense amplifier for detecting depolarization signals originating from an atrium;*

*a ventricular sense amplifier for detecting depolarization signals originating from only one ventricle;*

*pacing control circuitry, connected to the atrial sense amplifier, for starting an atrial-ventricular delay period when the atrial sense amplifier detects an atrial depolarization signal, and for inhibiting stimulation of the left ventricle and the right ventricle when a depolarization signal from the one ventricle is detected during the atrial-ventricular delay period; and*

*a stimulating circuit for stimulating the left ventricle and the right ventricle at the end of the atrial-ventricular delay period if a depolarization signal is not detected from the one ventricle during the atrial-ventricular delay period for effecting a coordinated contraction of ventricles contracting in an incoordinate manner to improve the pumping ability of the heart suffering from heart failure.*

*303. The heart failure treatment device of claim 302, further comprising an electrode adapted to be positioned through the coronary sinus to the left ventricle for stimulating the left ventricle.*

*304. The heart failure treatment device of claim 302, wherein the stimulating circuit generates pacing pulses for stimulating the left ventricle and the right ventricle.*

*305. The heart failure treatment device of claim 302, wherein the stimulation circuit stimulates the left ventricle substantially simultaneously with the stimulation of the right ventricle.*

*306. The heart failure treatment device of claim 302, wherein the one ventricle is the right ventricle.*

*307. The heart failure treatment device of claim 302, wherein the one ventricle is the left ventricle.*

*308. A method for improving the pumping ability of a heart suffering from heart failure comprising:*

*positioning a first electrode through the coronary sinus to the left ventricle;*

*positioning a second electrode in the right ventricle;*

*applying a pacing pulse to the left ventricle through the first electrode;*

*applying a pacing pulse to the right ventricle through the second electrode substantially simultaneously with application of the pacing pulse to the left ventricle, wherein the pacing pulses are applied to the left ventricle and the right ventricle at a programmed rate.*

*309. The method of claim 308, wherein the pacing pulses are applied at the programmed rate without regard to any sensing.*

*310. A method of improving the pumping ability of a heart suffering from heart failure comprising:*

*sensing for depolarization signals originating from a first ventricle; and*

*stimulating a second ventricle when a depolarization signal from the first ventricle is detected for effecting a coordinate contraction of ventricles contracting in an incoordinate manner to improve the pumping ability of the heart suffering from heart failure.*

*311. The method of 310, further comprising locating an electrode through the coronary sinus to the left ventricle.*

*312. The method of claim 310, wherein the second ventricle is stimulated within a period of time after detecting a depolarization signal from the first ventricle, the period of time being sufficient to effect a substantially simultaneous contraction of both ventricles.*

*313. The method of claim 312, wherein the second ventricle is stimulated within 10 milliseconds after detecting the depolarization signal of the first ventricle.*

*314. A method of improving the pumping ability of a heart suffering from heart failure comprising:*

*sensing for depolarization signals originating from a left ventricle;*

*sensing for depolarization signals originating from a right ventricle; and*

*stimulating the left ventricle and the right ventricle after a time period if a depolarization signal is not detected from either the left ventricle or the right ventricle during the time period for effecting a coordinated contraction of ventricles contracting in an incoordinate manner to improve the pumping ability of a heart suffering from heart failure.*

*315. A method of improving the pumping ability of a heart suffering from heart failure comprising:*

*sensing for depolarization signals originating from only one ventricle; and*

*stimulating a right ventricle and a left ventricle if a depolarization signal is not detected from the one ventricle during a time period for effecting a coordinated contraction of ventricles contracting in an incoordinate manner to improve the pumping ability of a heart suffering from heart failure.*

*316. A method for improving the pumping ability of a heart suffering from heart failure comprising:*

*sensing for depolarization signals origination in an atrium;*

*sensing for depolarization signals originating from a left ventricle;*

*sensing for depolarization signals originating from a right ventricle; and*

*stimulating the left ventricle and the right ventricle after a time period if a depolarization signal is not detected from either the left ventricle or the right ventricle during the time period for effecting a coordinated contraction of ventricles contracting in an incoordinate manner to improve the pumping ability of a heart suffering from heart failure.*

*317. The method of claim 316, further comprising stimulating the left ventricle and the right ventricle when a depolarization signal from either the left ventricle or the right ventricle is detected during the time period for effecting a coordinate contraction of the ventricles.*

*318. The method of claim 316, wherein the time period is an atrial-ventricular delay.*

*319. The method of claim 316, wherein the time period is a cardiac cycle interval.*

*320. The method of claim 316, further comprising locating an electrode through the coronary sinus to the left ventricle.*

*321. The method of claim 316, wherein stimulating the left ventricle and the right ventricle includes stimulating only one site in the left ventricle and only one site in the right ventricle.*

*322. The method of claim 316, wherein stimulating the left ventricle and the right ventricle includes applying a pacing pulse to the left ventricle and applying a pacing pulse to the right ventricle.*

*323. The method of claim 316, wherein stimulating the left ventricle and the right ventricle includes stimulating the left ventricle substantially simultaneously with stimulating the right ventricle.*

*324. A method for improving the pumping ability of a heart suffering from heart failure comprising:*

*sensing for depolarization signals origination in an atrium;*

*sensing for depolarization signals originating from only one ventricle; and*

*stimulating the left ventricle and the right ventricle after a time period if a depolarization signal is not detected from the one ventricle during the time period for effecting a coordinated contraction of ventricles contracting in an incoordinate manner to improve the pumping ability of a heart suffering from heart failure.*

*325. The method of claim 324, further comprising stimulating the left ventricle and the right ventricle when a depolarization signal from the one ventricle is detected during the time period for effecting a coordinated contraction of the ventricles.*

*326. The method of claim 324, wherein the time period is an atrial-ventricular delay.*

*327. The method of claim 324, wherein the time period is a cardiac cycle interval.*

*328. The method of claim 324, further comprising locating an electrode through the coronary sinus to the left ventricle.*

*329. The method of claim 324, wherein stimulating the left ventricle and the right ventricle includes stimulating only one site in the left ventricle and only one site in the right ventricle.*

*330. The method of claim 324, wherein stimulating the left ventricle and the right ventricle includes applying a pacing pulse to the left ventricle and applying a pacing pulse to the right ventricle.*

*331. The method of claim 324, wherein stimulating the left ventricle and the right ventricle includes stimulating the left ventricle substantially simultaneously with stimulating the right ventricle.*

* * * * *